(12) United States Patent
Anikeeva et al.

(10) Patent No.: US 9,861,810 B2
(45) Date of Patent: Jan. 9, 2018

(54) METHODS AND APPARATUS FOR STIMULATING AND RECORDING NEURAL ACTIVITY

(71) Applicants: Polina Olegovna Anikeeva, Somerville, MA (US); Xiaoting Jia, Somerville, MA (US); Chi Lu, Cambridge, MA (US); Andres Canales, Brighton, MA (US); Ulrich Paul Froriep, Brighton, MA (US); Christina Myra Tringides, Cambridge, MA (US); Yoel Fink, Brookline, MA (US)

(72) Inventors: Polina Olegovna Anikeeva, Somerville, MA (US); Xiaoting Jia, Somerville, MA (US); Chi Lu, Cambridge, MA (US); Andres Canales, Brighton, MA (US); Ulrich Paul Froriep, Brighton, MA (US); Christina Myra Tringides, Cambridge, MA (US); Yoel Fink, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1238 days.

(21) Appl. No.: 13/919,594

(22) Filed: Jun. 17, 2013

(65) Prior Publication Data

US 2014/0371564 A1    Dec. 18, 2014

Related U.S. Application Data

(63) Continuation of application No. PCT/US2013/046103, filed on Jun. 17, 2013.

(51) Int. Cl.
*A61B 5/04*    (2006.01)
*A61N 1/05*    (2006.01)
(Continued)

(52) U.S. Cl.
CPC .......... *A61N 1/0551* (2013.01); *A61B 5/0084* (2013.01); *A61B 5/04001* (2013.01);
(Continued)

(58) Field of Classification Search
CPC .. A61N 1/0551; A61N 1/0529; A61N 1/0531; A61N 1/0534; A61N 5/0601;
(Continued)

(56) References Cited

U.S. PATENT DOCUMENTS 4,928,689 A * 5/1990 Hauser ................. A61N 1/0565
607/2
5,411,527 A * 5/1995 Alt ....................... A61N 1/0587
600/374

(Continued)

OTHER PUBLICATIONS

Piironen et al. "Ultrasmall and Customizable Multichannel Electrodes for Extracellular Recordings" J Neurophysiol 105: 1416-1421 (Jan. 2011).*

(Continued)

*Primary Examiner* — Linda Dvorak
*Assistant Examiner* — Erin M Cardinal
(74) *Attorney, Agent, or Firm* — Cooley LLP

(57) ABSTRACT

Thermal drawing processes can be used to make multifunctional, high-resolution neural probes for neural recording and stimulation. An exemplary neural probe may include one or more conductive fibers or microelectrodes coated with two or more layers of insulating material, at least one of which is partially etched to expose a tip at the neural probe's distal end. The conductive fibers conduct electrical signals (e.g., neural spikes or electrical stimulation) between the tip and the neural probe's proximal end. Optional optical and fluidic waveguides may guide light and fluid, respectively, between the tip and the proximal end. A neural probe may be flexible enough for long-term (chronic) implantation in neural tissue (e.g., the brain) without excessive tissue (Continued)

damage, even during movement of the brain in the skull. The probe may be made from biocompatible materials, such as insulating and conductive polymers, that have negligible (insignificant) interaction with the surrounding tissue.

31 Claims, 24 Drawing Sheets

(51) Int. Cl.
 *A61N 5/06* (2006.01)
 *A61B 5/00* (2006.01)
(52) U.S. Cl.
 CPC .......... *A61B 5/4064* (2013.01); *A61B 5/6868* (2013.01); *A61N 1/0529* (2013.01); *A61N 5/0601* (2013.01); *A61N 5/0622* (2013.01); *A61M 2202/09* (2013.01); *A61M 2207/00* (2013.01); *A61N 2005/063* (2013.01); *A61N 2005/0662* (2013.01)
(58) Field of Classification Search
 CPC ................ A61N 5/0622; A61B 5/0084; A61B 5/04001; A61B 5/4064; A61B 5/6868; A61B 2562/028; A61B 2562/0285
 USPC ........................................................ 600/377
 See application file for complete search history.

(56) References Cited

U.S. PATENT DOCUMENTS

| | | | | |
|---|---|---|---|---|
| 5,716,391 | A * | 2/1998 | Grandjean | A61N 1/0573 607/126 |
| 6,091,979 | A * | 7/2000 | Madsen | A61B 5/4094 600/377 |
| 6,304,784 | B1 | 10/2001 | Allee et al. | |
| 8,005,526 | B2 * | 8/2011 | Martin | A61B 5/0408 600/372 |
| 2005/0053345 | A1 | 3/2005 | Bayindir et al. | |
| 2007/0060815 | A1 * | 3/2007 | Martin | A61B 5/0408 600/372 |
| 2007/0167815 | A1 * | 7/2007 | Jacobsen | A61N 1/0529 600/459 |
| 2009/0099441 | A1 * | 4/2009 | Giszter | A61N 1/0529 600/377 |
| 2009/0292325 | A1 * | 11/2009 | Cederna | A61N 1/05 607/2 |
| 2009/0299166 | A1 | 12/2009 | Nishida et al. | |
| 2010/0114272 | A1 * | 5/2010 | Haidarliu | A61B 5/04001 607/115 |
| 2011/0087315 | A1 * | 4/2011 | Richardson-Burns | A61B 5/0408 607/116 |
| 2011/0112503 | A1 * | 5/2011 | Ismagilov | B01L 3/502715 604/500 |
| 2011/0257501 | A1 * | 10/2011 | Huys | A61N 1/0551 600/377 |
| 2012/0323288 | A1 | 12/2012 | Anderson et al. | |
| 2013/0030274 | A1 | 1/2013 | Jamieson et al. | |
| 2013/0131482 | A1 | 5/2013 | Fedder et al. | |

OTHER PUBLICATIONS

Rutten et al., "Neuroelectronic Interfacing With Cultured Multielectrode Arrays Toward a Cultured Probe" Proceedings of the IEEE, vol. 89(7), pp. 1013-1029 (2001).*
International Search Report for International Application No. PCT/US2013/046103, dated Mar. 26, 2014, 4 pages.
A. Canales, et al., "Fiber-Inspired Optoelectronic Devices for Neural Recording and Stimulation," presented Oct. 14, 2012.
Amarjit Singh, et al., "Improving Mechanical Stiffness of Coated Benzocyclobutene (BCB) Based Neural Implant", IEEE, 2004, pp. 4298-4301.
Andres Canales, et al., "Fiber-Inspired Devices for Neural Probes", Department of Materials Science and Engineering, presented Nov. 28, 2012.
Anikeeva, P.O. et al., "Optetrode: a multichannel readout for optogenetic control in freely moving mice," Nat. Neurosci. 15, 163-170, (2011).
Anita F. Quigley, et al., "A Conducting-Polymer Platform with Biodegradable Fibers for Stimulation and Guidance of Axonal Growth", Adv. Mater. 2009, 21, 4393-4397.
Axel Blau, et al., "Flexible, all-polymer microelectrode arrays for the capture of cardiac and neuronal signals", Biomaterials 32 (2011) 1778-1786.
Burak Temelkuran, et al., "Wavelength-scalable hollow optical fibres with large photonic bandgaps for C02 laser transmission" Nature, vol. 420, Dec. 12, 2002, pp. 650-653.
D. S. Deng et al., "Novel fabrication and optoelectronic property of semiconductor filaments by optical fiber thermal drawing," Nanoengineering: Fabrication, Properties, Optics, and Devices VI. Ed. Elizabeth A. Dobisz & Louay A. Eldada. San Diego, CA, USA: SPIE, 2009. 740204-3.
Dong-Hwan Kim, et al., "Conducting polymers on hydrogel-coated neural electrode provide sensitive neural recordings in auditory cortex", Acta Biomaterialia 6 (2010) 57-62.
Dufour S, Lavertu G, Dufour-Beauséjour S, Juneau-Fecteau A, Calakos N, Deschênes M, Vallée R, De Koninck Y. 2013. "A Multimodal Micro-Optrode Combining Field and Single Unit Recording, Multispectral Detection and Photolabeling Capabilities.." PloS One 8 (2): e57703.
E K Purcell, et al., "In vivo evaluation of a neural stem cell-seeded prosthesis", J. Neural Eng. 6 (2009) 026005 (10pp).
Gradinaru, V. et al., "Molecular and Cellular Approaches for Diversifying and Extending Optogenetics," Cell 141, 154-165 (2010).
Haixin Zhu, et al., "High-Yield Benzocyclobuten (BCB) Based Neural Implants for Simultaneous Intra-and Extracortical Recording in Rats", Proceedings of the 26th Annual International Conference of the IEEE EMBS, Sep. 1, 2004, pp. 4341-4344.
J P Harris, et al., "Mechanically adaptive intracortical implants improve the proximity of neuronal cell bodies", J. Neural Eng. 8 (2011) 066011 (13 pp).
Jiayi Zhang, et al., "Integrated device for optical stimulation and spatiotemporal electrical recording of neural activity in light-sensitized brain tissue", J. Neural Eng. 6 (2009) 055077 (13pp).
Jing Wang, et al., "Integrated device for combined optical neuromodulation and electrical recording for chronic in vivo applications", J. Neural Eng. 9 (2012)016001 (14 pp).
John P. Seymour, et al., "Novel multi-sided, microelectrode arrays for implantable neural applications", Biomed Microdevices (2011) 13: 441-451.
Jonathan T. W. Kuo, et al., "Novel flexible Parylene neural probe with 3D sheath structure for enhancing tissue integration", Lab on a Chip, DOI: 10.1039/c2lc40953f, 2012.
Keekeun Lee, et al., "Biocompatible benzocyclobutene-based intracortical neural implant with surface modification", Institute of Physics Publishing, J. Micromech. Microeng. 15 (2005) 2149-2155.
Kee-Kuen Lee, et al., "Polyimide-based intracortical neural implant with improved structural stiffness", J. Micromech. Microeng. 14 (2004) 32-37.
Laura K. Povlich, et al., "Synthesis, copolymerization and peptide-modification of carboxylic acid-functionalized 3,4-ethylenedioxythiophene (EDOTacid) for neural electrode interfaces", Biochimica et Biophysica Acta (2012) http://dx.doi.org/10.1016/j.bbagen.2012.10.017.
LeChasseur Y, Dufour S, Lavertu G, Bolles C, Deschenes M, Vallée R, De Koninck Y. 2011. "A Microprobe for Parallel Optical and Electrical Recordings From Single Neurons in Vivo." Nature Methods 8 (4) (Feb. 13): 319-325.
Mohammad Reza Abidian, et al., "Conducting-Polymer Nanotubes Improve Electrical Properties, Mechanical Adhesion, Neural Attachment and Neurite Outgrowth of Neural Electrodes", small 2010, 6, No. 3, 421-429.
P. Anikeeva, "Fiber-Inspired Optoelectronic Devices for Neural Recording and Stimulation", Department of Materials Science and Engineering, presented on Jun. 18, 2012.

(56) References Cited

OTHER PUBLICATIONS

Paul M. George, et al., "Fabrication and biocompatibility of polypyrrole implants suitable for neural prosthetics", Biomaterials 26 (2005) 3511-3519.
Polina Anikeeva, "Fiber-Inspired Optoelectronic Devices for Neural Recording and Stimulation", Department of Materials Science and Engineering, MIT, presented Jun. 18, 2012.
Polina Anikeeva, "High-Resolution Optoelectronic Neural Interfaces", Department of Materials Science and Engineering, presented Nov. 29, 2012.
Polina Anikeeva, "Optoelectronics for Neural Recording and Stimulation", Department of Materials Science and Engineering, presented Oct. 27, 2012.
Polina Anikeeva, "Optoelectronics for Neural Recording and Stimulation", Dept. of Materials Science and Engineering, presented Mar. 30, 2012.
Rubehn B, Wolff SBE, Tovote P, Lüthi A, Stieglitz T. 2013. "A Polymer-Based Neural Microimplant for Optogenetic Applications: Design and First in Vivo Study." Lab on a Chip (Jan. 10).
S. Metz, et al., "Flexible polyimide probes with microelectrodes and embedded microfluidic channels for simultaneous drug delivery and multi-channel monitoring of bioelectric activity", Biosensors and Bioelectronics 19 (2004) 1309-1318.
Sarah M. Richardson-Burns, et al., "Electrochemical polymerization of conducting polymers in living neural tissue", J. Neural Eng. 4 (2007) L6-L13.
Sebastien Royer, et al., "Multi-array silicon probes with integrated optical fibers: light-assisted perturbation and recording of local neural circuits in the behaving animal", European Journal of Neuroscience, vol. 31, pp. 2279-2291, 2010.
Seth A. Hara, et al., "Pre-Implantation Electrochemical Characterization of a Parylene C Sheath Microelectrode Array Probe", IEEE, 2012, pp. 5126-5129.
Shoji Takeuchi, et al., "Parylene Flexible Neural Probe with Micro Fluidic Channel", IEEE, 2004, pp. 208-211.
Stephanie P. Lacour, et al., "Flexible and stretchable micro-electrodes for in vitro and in vivo neural interfaces", Med Biol Eng Comput (2010) 48: 945-954.
Tae-il Kim, et al., "Injectable, Cellular-Scale Optoelectronics with Applications for Wireless Optogenetics", Science, vol. 340, 211 (2013) pp. 211-216.
Takashi D. Yoshida Kozai, et al., "Ultrasmall implantable composite microelectrodes with bioactive surfaces for chronic neural interfaces", Nature Materials, vol. 11, Dec. 2012, pp. 1065-1073.
Yi Lu, et al., "Poly(vinyl alcohol)/poly(acrylic acid) hydrogel coatings for improving electrode-neural tissue interface", Biomaterials 30 (2009) 4143-4151.
Zhang, F. et al., "Multimodal fast optical interrogation of neural circuitry," Nature 446, 633-641 (2007).
International Written Option for International Application No. PCT/US2013/046103, dated Mar. 26, 2014, 7 pages.

\* cited by examiner

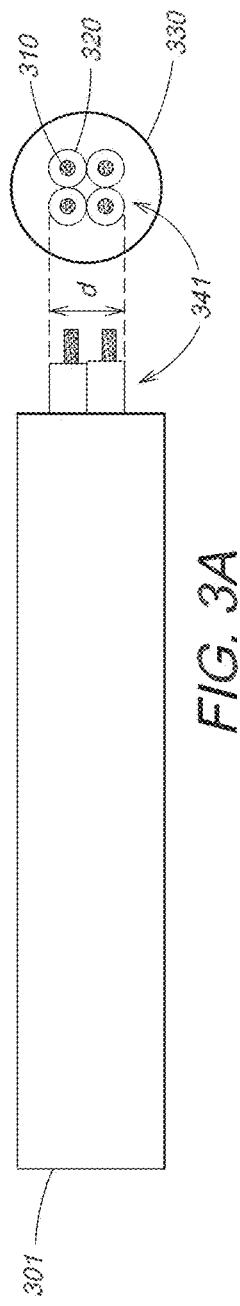
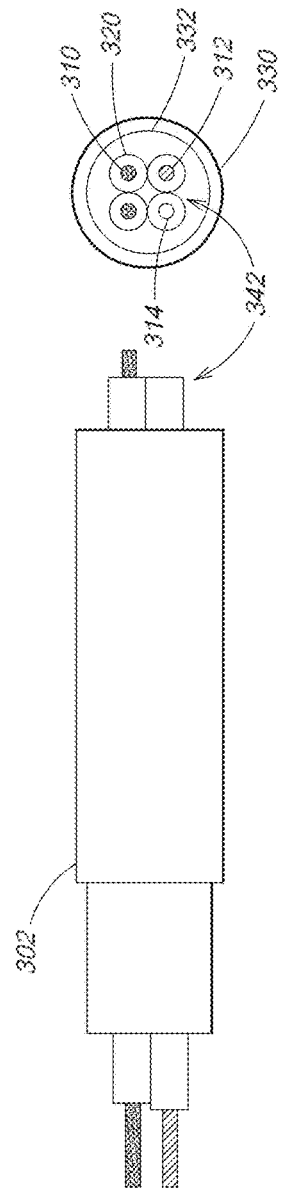
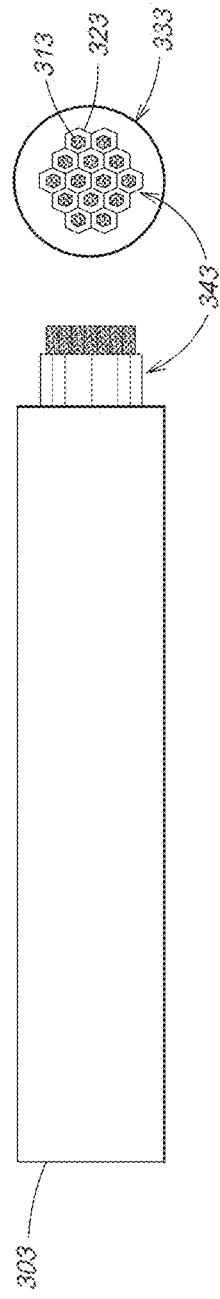
FIG. 3A
FIG. 3B
FIG. 3C

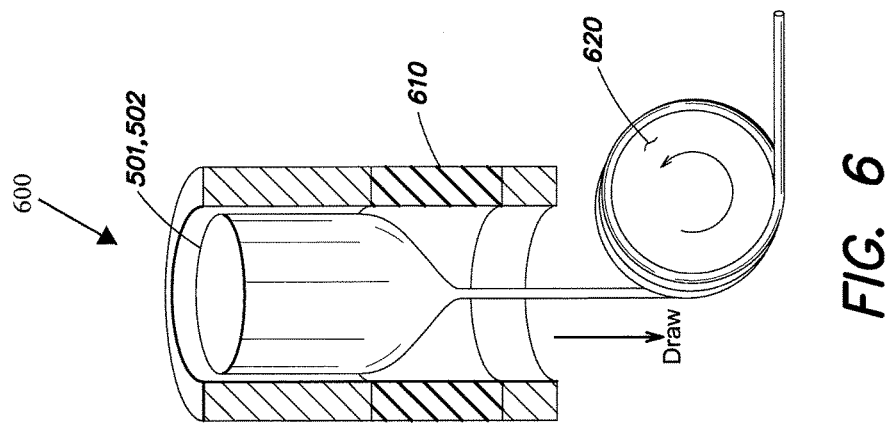
FIG. 6
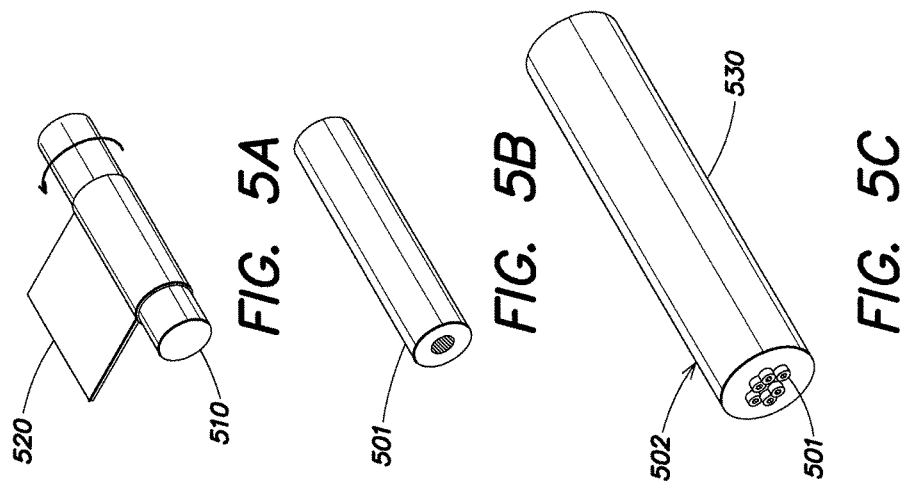
FIG. 5A
FIG. 5B
FIG. 5C

METHODS AND APPARATUS FOR STIMULATING AND RECORDING NEURAL ACTIVITY

CROSS-REFERENCE TO RELATED APPLICATION

This application claims the priority benefit as a bypass continuation, under 35 U.S.C. §120, of PCT/US2013/046103, filed Jun. 17, 2013, and entitled "Methods and Apparatus for Stimulating and Recording Neural Activity."

GOVERNMENT SUPPORT

This invention was made with government support under Grant No. DMR-0819762 awarded by the National Science Foundation. The government has certain rights in this invention.

BACKGROUND

Neural probes are used to record and stimulate neural activity in vivo in neural tissue, including the brain. As understood by those of skill in the art, stimulating a neuron causes a brief change in the neuron's electrical membrane potential. The change in membrane potential, also called a nerve impulse or spike, plays an important role in cell-to-cell communication and can be detected using electrodes inserted or implanted in the neural tissue. Relatively low-impedance (e.g., less than about 150 kΩ) electrodes can be used to record the local field potential (LFP), which is the low-frequency component of the extracellular voltage detected in the cortex. Electrodes with higher impedance (e.g., about 150 kΩ to about 10 MΩ) can be used to record the unit potential, which is the electrical activity of a single neuron. Implanted electrodes can also be used to stimulate neural activity. Conventional technologies for in vivo neural recording and stimulation include silicon multi-electrode arrays (MEAs), individual metallic electrodes, metal microwire tetrodes and stereotrodes, silicon multitrode probes, cone electrodes, and flat recording arrays embedded in polymer or a silk matrix.

SUMMARY

The Inventors have recognized that conventional technologies for in vivo neural recording and stimulation suffer from several drawbacks. More specifically, conventional devices for electrophysiological recording on the single cell level have elastic moduli that are much higher than the elastic modulus of neural tissue (e.g., tens to hundreds of gigapascals versus kilopascals to megapascals). In other words, conventional electrophysiological recording devices tend to be much stiffer than neural tissue. Because they are stiffer than neural tissue, conventional electrophysiological recording devices may damage tissue during and after implantation in neural tissue. The tissue damage causes the formation of glial scars, neuronal death, and bleeding, all of which contribute to a progressive decrease in the quality of the neural recording (e.g., lower signal-to-noise ratio (SNR), fewer monitored cells). As a result, with a conventional electrophysiological recording devices, it may become impossible to record single neuron activity reliably within several months of implantation.

It is also difficult to integrate other devices with conventional electrophysiological recording devices. For example, conventional electrophysiological recording devices do not allow for straightforward incorporation of other elements that may facilitate neural stimulation functions, such as optical waveguides (e.g., for optogenetic experiments or imaging) and hollow channels (e.g., for drug delivery and fluid sampling).

Thus, drawbacks including excessive stiffness and limited engineering design options limit the usefulness of conventional neural recording device for treating disease and conducting basic scientific studies of neural circuits.

In view of the foregoing, embodiments of the present invention address the shortcomings of conventional neural recording devices. One embodiment includes a neural probe with at least one outer insulating layer, at least one inner insulating layer, and at least one conductive fiber. The inner insulating layer is disposed within the outer insulating layer and projects out of the outer insulating layer to form a tip at a distal end of the neural probe with an outer diameter of less than about 500 µm. The conductive fiber is disposed with the inner insulating layer and conduct electrical signals between the proximal and distal ends of the neural probe.

In some examples, the neural probe comprises a plurality of conductive fibers, each of which is disposed within a respective inner insulating layer. In these cases, a soluble adhesive, disposed on a surface at the tip of the neural probe, may secure a first conductive fiber in the plurality of conductive fibers to a second conductive fiber in the plurality of conductive fibers during insertion of the neural probe into tissue. After insertion/implantation, the soluble adhesive may dissolves, allowing the conductive fibers to splay apart and/or move in a less constrained fashion while implanted.

The conductive fiber may be made of tin, tin-indium, tin-silver, tin-gold, tin-zinc, gold, silver, platinum, iridium, tungsten, conductive polyethylene, conductive polycarbonate, conductive polyurethane, or a combination thereof. It may have an impedance at the distal end of the neural probe of about 150 kΩ to about 10 MΩ (e.g., about 150 kΩ to about 3 MΩ). In some cases, the conductive fiber's impedance is selected to measure the local field potential (LFP); in other cases, it is selected to measure the single-unit potential.

The inner insulating layer, outer insulating layer, or both the inner and outer insulating layers may comprise one or more polymers. In some cases, the inner insulating layer has a first solubility and the outer insulating layer has a second solubility different than the first solubility. In other cases, the inner insulating layer has a first molecular weight and the at least one outer insulating layer has a second molecular weight different than the first molecular weight. Differences in solubility and/or molecular weight may be used to selectively or preferentially etch one insulating layer (e.g., the outer insulating layer) without etching the other insulating layer (e.g., the inner insulating layer).

An exemplary neural probe may also include at least one optical fiber, disposed within the at least one outer insulating layer, to guide light between the proximal end of the neural probe and the distal end of the neural probe. It can also define a hollow lumen, disposed within the at least one outer insulating layer, to guide fluid between the proximal end of the neural probe and the distal end of the neural probe. If desired, the neural probe may also include at least one mammalian cell, disposed within about 500 µm of the distal end of the neural probe, to interact with neural tissue. For instance, the cell may be disposed on the tip or within a lumen or cavity at the tip. Such a neural probe may also include a channel defined by the conductive fiber, an optical fiber, or a hollow lumen to stimulate the mammalian cell and/or record the mammalian cell's physiological response to interaction with the neural tissue.

Additional embodiments include a method of making a neural probe using thermal drawing. First, a first insulating material is disposed about an outer surface of at least one conductive rod so as to form a first pre-form, e.g., by wrapping, dip-coating, spraying, sputtering, or depositing the first insulating material on the conductive rod. The conductive rod can also be inserted into a lumen formed by the first insulating material. Next, a second insulating material, different than the first insulating material, is disposed about an outer surface of the first pre-form so as to form a second pre-form. The second pre-form is drawn to form a coated conductive fiber. At least a portion of the second insulating material is removed from a distal end of the coated conductive fiber so as to form the neural probe.

In some cases, the second pre-form is formed by drawing the first pre-form to form a drawn pre-form, sectioning the drawn pre-form into a plurality of segments, and disposing the second insulating material about at least some of the plurality of segments to form the second pre-form. The second insulating material may also be disposed about an outer surface of an optical fiber pre-form and/or about an outer surface of a structure (e.g., a mandrel) that can be used to define a hollow lumen.

Drawing the second pre-form may include heating the second pre-form to a first temperature above both the second pre-form's melting temperature and its glass transition temperature. The second pre-form is then heated to a second temperature below the first temperature before being drawn at a predetermined drawdown ratio, e.g., by applying a stress of about 150 g/mm$^2$ to about 1.5 kg/mm$^2$ to the polymer-coated pre-form. In some cases, the first temperature may be about 30% to about 80% above the higher of the melting temperature and the glass transition temperature, and the second temperature is about 5% to about 30% above the higher of the melting temperature and the glass transition temperature.

Once the fiber is drawn, the neural probe's tip may be defined using any suitable method for selectively removing the second insulating material. For instance, at least a portion of the second insulating material can be dissolved in a solvent, etching away, or removed based on a difference in molecular weight between the first insulating layer and the second insulating layer. If desired, at at least one mammalian cell may be disposed within about 500 µm of the distal end of the neural probe, e.g., placing the cell on the tip or inserting the cell into a hollow lumen or cavity via suction, capillary action, or electromagnetic force.

Yet another embodiment includes a method of interfacing with neural tissue with an exemplary neural probe, which may include a conductive fiber disposed inside an inner insulating layer, which in turn is disposed within an outer insulating layer. A researcher, technician, or physician inserts a distal end of a neural probe into neural tissue such that the neural probe's tip, which has an outer diameter of less than about 500 µm, interfaces with the tissue. Once properly inserted, the conductive fiber conducts electrical signals between the proximal and distal ends of the neural probe.

A recording system may record the electrical signals conducted by the neural probe. Similarly, the neural probe may deliver electrical stimulation via the conductive fiber. It may also guiding light between the proximal end of the neural probe and a selected portion of the neural tissue via an optical fiber disposed within the neural probe's outer insulating layer. And it can convey fluid (e.g., drugs) to or from a selected portion of the neural tissue via a hollow lumen disposed within the outer insulating layer. The neural probe may also guide an electromagnetic signal or a chemical that stimulates at least one mammalian cell disposed on or in the neural probe within about 500 µm from the neural probe's distal end.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 3A-3D illustrate different neural probe configurations suitable for use with the system of FIG. 1.

FIGS. 5A-5C illustrate a process for coating a conductive rod in an insulating material (FIG. 5A) to form a first pre-form (FIG. 5B), which is in turn coated with another insulating material to form a second pre-form (FIG. 5C) suitable for thermal drawing.

FIG. 6 illustrates a process for drawing the second pre-form shown in FIG. 5C.

DETAILED DESCRIPTION

Figure 1:
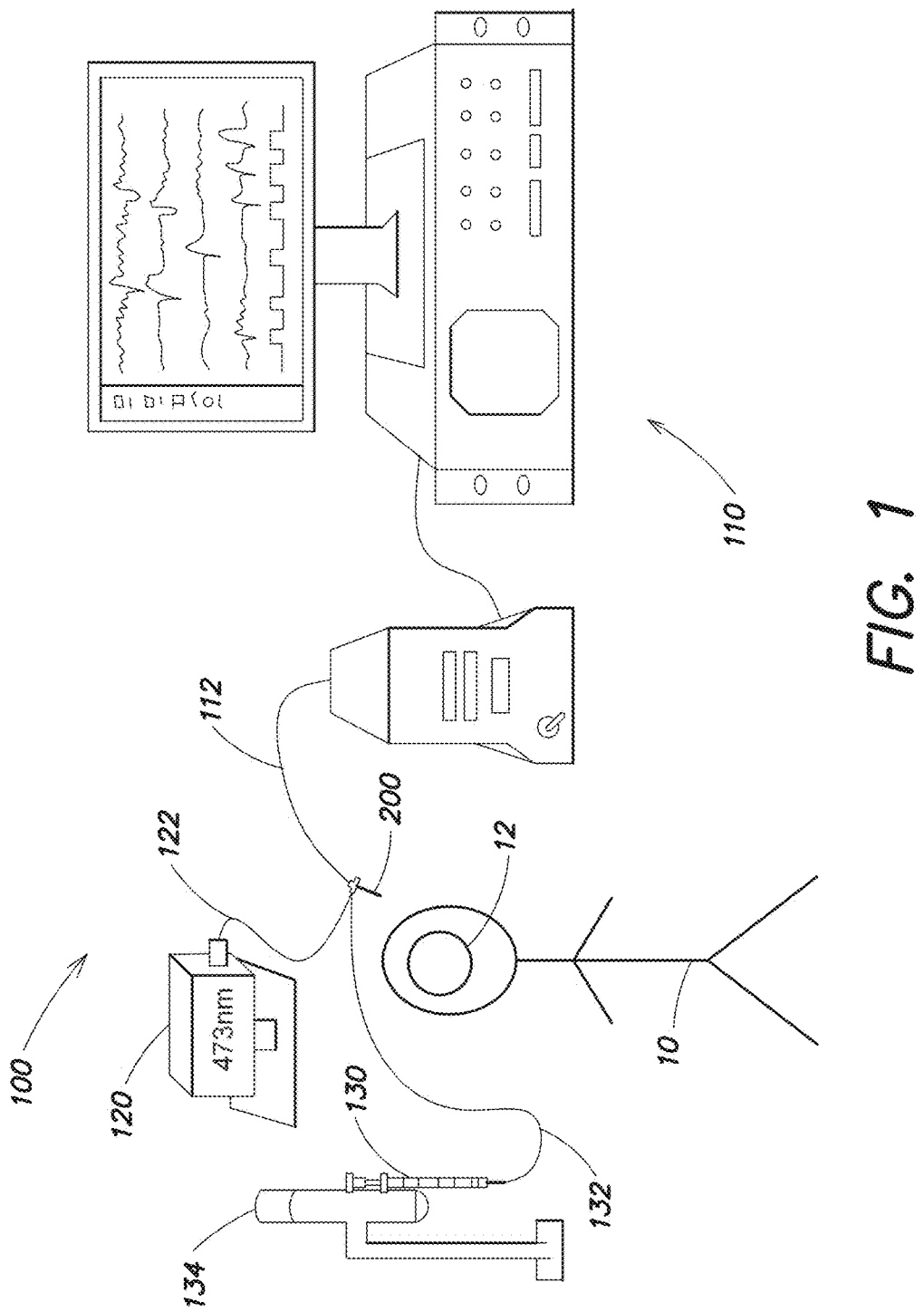
FIG. 1 illustrates a system for recording and stimulating electrical activity in neural tissue using a flexible neural probe.

Embodiments of the present invention include fiber-inspired probes for stimulating and recording neural activity using electrical, optical, and pharmacological interrogation. Exemplary neural probes can be implanted in human patients and animal models to assess and modulate neural activity in the context of diseases such as epilepsy, Parkinson's, Alzheimer's, major depressive disorder, autism spectrum disorders, substance addiction, post-traumatic stress disorder, and traumatic brain injury. They can also be used to research basic principles of brain function, including but not limited to learning and memory processes. Furthermore, an exemplary neural probe can be used in a brain-machine interface to restore motor and cognitive function lost due to limb amputation, locked-in syndrome, paraplegia, or quadriplegia resulting from spinal cord or peripheral nerve injury.

An exemplary neural probe can be made using a thermal drawing process similar to the drawing processes used for making optical fibers. For instance, thermal drawing can be used to make a neural probe that includes an array of metal or conductive polymer wires within an insulating cladding, which insulates each individual wire and the device as a whole. Suitable materials for the insulating cladding include, but are not limited to poly(etherimide), polycarbonate, poleolefin, cyclic olefin copolymer, polysulfone, polyurethane, glasses (e.g., silica), and derivatives thereof. The geometry of the wires, the pattern of the array, and the geometry of the cladding can vary, and may be similar the fiber-like shape of a nerve bundle. A neural probe can also include a hollow channel enabling drug delivery and an optical waveguide for optogenetic stimulation or imaging.

Systems for High-Resolution Neural Recording and Stimulation

FIG. 1 illustrates a system 100 for recording and/or stimulating neural activity in a person or animal (not shown). The system 100 includes a neural probe 200 that can be inserted and chronically implanted in neural tissue 12 of a subject 10. The neural probe 200 is electrically connected to a multi-channel data acquisition system 110 via a cable 112, which conveys electrical signals representative of neural activity (e.g., single unit potentials and/or local field potentials) to the data acquisition system 110, which records and optionally analyzes the signals. The data acquisition system 110 may also generate electrical stimulation signals and transmit them to selected neurons within the neural tissue 112 via the cable 112 and the neural probe 200.

The neural probe 200 is optically coupled to a light source, shown in FIG. 1 as a laser diode 120, via an optical fiber 122. The optical fiber 122 guides electromagnetic radiation (light) from the laser diode 120 to neural probe 200 for stimulation of the neural tissue 12. For instance, the laser diode 120 may emit pulses of blue light (473 nm) for optogenetic stimulation of specific neurons in the neural tissue 12 that express light-sensitive proteins. For instance, optogenetic stimulation may be used as part of a brain-machine interface to induce certain reactions in the patient, possibly to compensate for loss of or damage to neural tissue 12. The neural probe 120 may also guide light from the neural tissue 12 to a detector (not shown), e.g., to image the neural tissue 12 or to measure transmission/scattering of light through neural tissue 12.

In addition, the neural probe 200 may also be in fluid communication with a syringe 130 via tubing 132. Depressing the syringe's plunger with a syringe pump 134 causes fluid, such as a particular drug, to flow from the syringe 130 to the neural tissue 12 via the tubing 132 and the neural probe 200. Withdrawing the syringe's plunger with the syringe pump 134 sucks fluid out of the neural tissue 12 via the tubing 132 and the neural probe 200. The precise fluid speeds, fluid forces, and amounts of fluid can be controlled by adjusting the syringe pump as desired.

Flexible, High-Resolution Neural Probes

Figure 2A:
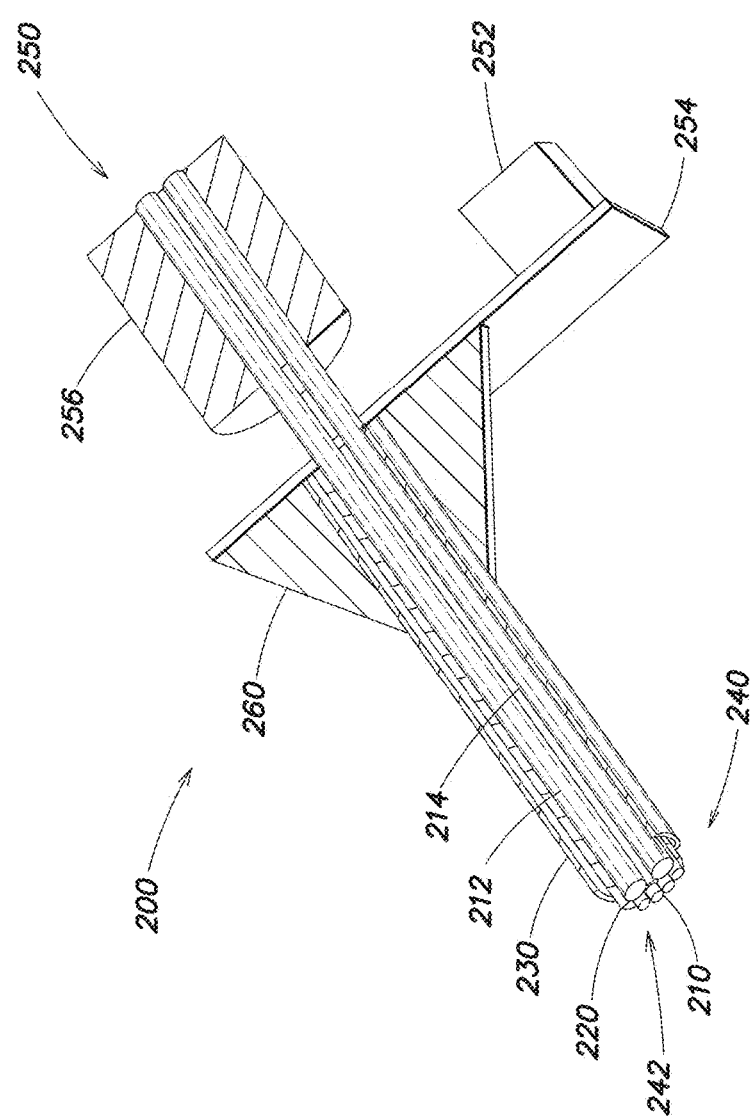
FIGS. 2A and 2B show cut-away and perspective views, respectively, of a neural probe suitable for use with the system of FIG. 1.
Figure 2B:
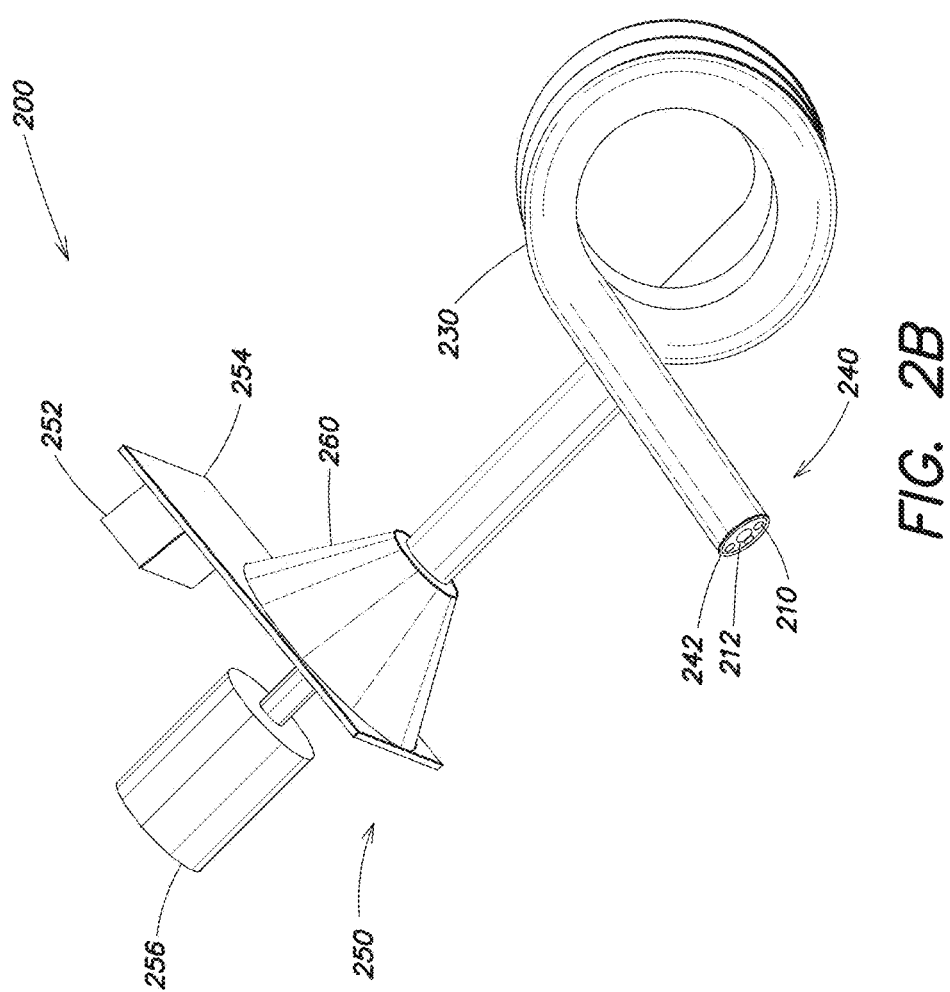

FIGS. 2A and 2B show cut-away and perspective views, respectively, of a neural probe 200 suitable for use with the neural recording/stimulation system 100 shown in FIG. 1.

The neural probe 200 is a flexible, multi-layer device made of biocompatible material, such as insulating and/or conductive polymers, using fiber-drawing techniques. Its length may range from a few centimeters to several meters, depending on the application. In some cases, the neural probe has a Young's modulus of tens of kilopascals to hundreds of megapascals (e.g., 35 MPa), which is a range commensurate with the Young's modulus of neural tissue. Because the neural probe's elastic modulus is commensurate with the elastic modulus of neural tissue, the neural probe 200 is less likely to damage neural tissue during insertion or while implanted than conventional implantable/insertable electrophysiological recording devices. It is also better suited to chronic, or long-term, implantation than conventional implantable/insertable electrophysiological recording devices.

As explained in greater detail below, the neural probe 200 includes at least one inner layer 220 and at least one outer layer 230 of biocompatible material disposed about one or more microelectrodes, or conductive fibers 210. The conductive fibers 210, which are thin wires or filaments, extend from the neural probe's proximal end 250 to its distal end 240 and may be fused together with the inner layer 220 and outer layer 230 during the drawing process.

The outer layer 230 may be at least partially etched or removed to form a tip 242 at the neural probe's distal end 240. For example, a portion of the outer layer 230 may be removed as described below to reduce the tip's outer diameter to about 500 µm or less (e.g., 252 µm, 125 µm, 100 µm, 75 µm, 50 µm, 25 µm, or smaller), Because the tip 242 is relatively small, it can be inserted relatively deeply into neural tissue (e.g., the brain) without unduly or excessively damaging the tissue during insertion or after implantation.

In operation, the conductive fibers 210 conduct electrical signals between the neural tissue and the neural probe's proximal end 250. As shown in FIG. 2, each conductive fiber 210 extends from the neural probe's proximal end 250 to its tip 242. In alternative embodiments, one or more of the conductive fibers 210 may be etched or trimmed back from the neural probe's tip 242, e.g., to be flush with the tip 242 or to create a recess in the tip 242. Exemplary conductive fibers 210 may have diameters of about 1 µm (about the size of a neuron) to about 20 µm (e.g., 5 µm, 10 µm, or 15 µm).

Each conductive fiber 210 may have an impedance chosen for the application at hand. For example, conductive fibers 210 with an impedance of less than about 150 k$\Omega$ can be used to measure the local field potential, whereas conductive fibers 210 with an impedance of about 150 k$\Omega$ to about 10 M$\Omega$ (e.g., 3 M$\Omega$ or 5 M$\Omega$) can be used to measure the unit potential, which represents the electrical activity of a single cell. As understood by those of skill in the art, the conductive fibers 210 made of metal (e.g., tin, tin-indium, tin-silver, tin-gold, tin-zinc, gold, silver, platinum, iridium, or tungsten) have an impedance that varies with diameter: in general, increasing the fiber diameter decreases the impedance for given length. Polymer-based conductive fibers 210 (e.g., fibers made of conductive (carbon-loaded) polyethylene, conductive polycarbonate, or conductive polyurethane) have an impedance that varies with size and composition: increasing the fiber diameter or the carbon loading decreases the impedance for given length.

The neural probe's proximal end 250 includes an electrical connector 252 that is coupled to the conductive fibers 210 via an electrode interface board 254. The electrical connector 252 can be or include any suitable type of connector, including one or more pin connectors, ZIF connectors, and/or Omnetics connectors. The electrical interface board 254 nay be a circuit (e.g., on a printed circuit board) with pads to which the microelectrodes are bonded.

The electrical connector 252 includes one or more pins that can be electrically coupled to an oscilloscope, spectrum analyzer, or other electronic measurement device that measures electrical signals conducted by the conductive fiber(s) 210 from the neural tissue. These signals may be recorded for later analysis (e.g., for fundamental research), analyzed in real-time (e.g., for operation of a brain-machine interface), or both. The connector 252 may also include one or more connections for a electronic signal generator, such as an arbitrary waveform generator, that produces signals suitable for stimulating one or more neurons in the neural tissue.

The neural probe 200 may also include an optical waveguide 212 and lumen 214 that each extend between the distal end 240 and the proximal end 250. The optical waveguide 212 may be formed of a glass or polymer optical fiber or other waveguide that supports propagation of one or more transverse modes at wavelengths in the ultraviolet, visible, and/or infrared portions of the electromagnetic spectrum. Similarly, the lumen 214 may be a channel defined by one or more hollow tubes made of polymer or other flexible, biocompatible material.

At the proximal end 250, the optical waveguide 212 and the lumen 214 terminate in an optical/fluidic coupler 256 with optical and fluid connections (not shown). The optical connections may be compatible with standard fiber-optic connectors, such as FC-PC, FC-APC, or FC-UPC connectors, for fiber-coupled light sources (e.g., lasers, light-emitting diodes, or lamps) and fiber-coupled detectors. Alternatively, or in addition, the optical/fluidic coupler 256 may also include integrated optical components, such as diode light sources and detectors, that receive or transmit light via the optical waveguide 212.

FIGS. 2A and 2B also show a drive 260 that extends circumferentially about the neural probe's proximal end 250. The drive 260 allows the implanted neural probe 200 to be lowered or raised as desired. In one example, the drive 260 raises and lowers the neural probe 200 by rotating a thumbscrew attached to a plastic housing that is fixed on the subject. Rotating the thumbscrew moves a vented screw, to which the neural probe 200 is attached, up or down. For a more detailed description of an example drive, please see P. Anikeeva et al., "Optetrode: a multichannel readout for optogenetic control in freely moving mice," Nature Neuroscience 15, 163-170 (2012), which is hereby incorporated herein by reference.

FIGS. 3A-3C show side (left) and end (right) views of additional neural probe configurations suitable for use with the neural stimulation/recording system 100 shown in FIG. 1. The neural probe 301 shown in FIG. 3A includes several conductive fibers 310, each of which is disposed within a respective inner layer 320 of biocompatible insulating material. Although FIG. 3A shows four conductive fibers 310 arranged in a square lattice, those of ordinary skill in the art will readily appreciate that other numbers and geometries of conductive fibers 310 are also possible. For instance, the coated conductive fibers 310 could be disposed in a triangular or hexagonal lattice; along the perimeter of a circle or polygon; in a sparse or random array; or in any other suitable arrangement.

The neural probe 301 also includes an outer layer 330 of biocompatible insulating material, such as poly(etherimide) or another suitable polymer, disposed about the inner layers 320. The inner layers 320 and outer layer 330 may be fused together during the drawing process, with a portion of the outer layer 320 is selectively etched away to expose a tip 341 with a diameter d at one end of the neural probe 301. The inner layers 320 may also be partially etched away to expose the conductive fibers 310. As shown in FIG. 3A, the tip's maximum diameter d depends on both the outer radius of the inner layers 320 and the geometry of the fiber arrangement.

FIG. 3B shows a neural probe 302 that includes an optical fiber 312 and a hollow lumen 314 in addition to conductive fibers 310. Like the conductive fibers 310, the optical fiber 312 and the conductive lumen 314 are each disposed within a respective inner layer 320 of insulating material, such as a flexible, biocompatible polymer. The optical fiber 312 transmits light between the proximal and distal ends of the neural probe 302, e.g., for optogenetic stimulation or sensing. The lumen 314 conveys fluid between the ends of the neural probe 302. For instance, the lumen 314 may convey a drug to the neural tissue. It may also be used to suction fluid from the neural tissue.

The neural probes also includes an optional intermediate layer 332, which is disposed between the inner layers 320 and the outer layer 330. The intermediate layer 332 and outer layer 330 may be etched to form a tip 342 with protruding inner layers 320. If desired, the inner layers 320 may be etched away as well to expose the conductive fibers 310. They may also be cleaved or polished flat, e.g., to protect the optical fiber 312, which might otherwise bend or break within the neural tissue. Alternatively, the optical fiber's tip may be exposed and polished or shaped (e.g., in the shape of a hemisphere) to enhance illumination of the neural tissue.

Although FIG. 3B shows two conductive fibers 310 arranged in a square lattice with the optical fiber 312 and the lumen 314, those of skill in the art will readily appreciate that other configurations are also possible. For instance, a neural probe may include conductive fibers and an optical fiber (but no lumen) or conductive fibers and a lumen (but no optical fiber). Similarly, a neural probe may include different numbers or arrangements of conductive fibers, optical fibers, and lumens. In another instance, the conductive fibers may be arranged concentrically about the optical fiber and/or the lumen, e.g., to facilitate recording of optically or chemically stimulated neural activity.

FIG. 3C shows a neural probe 303 with conductive fibers 313 whose cross sections are hexagonal. Each hexagonal conductive fiber 313 is disposed within a respective hexagonal inner layer 323 and arranged in a hexagonal lattice. The inner layers 320 are partially covered by an outer layer 333 that extends to within a few millimeters of the neural probe's tip 343.

Figure 3D:
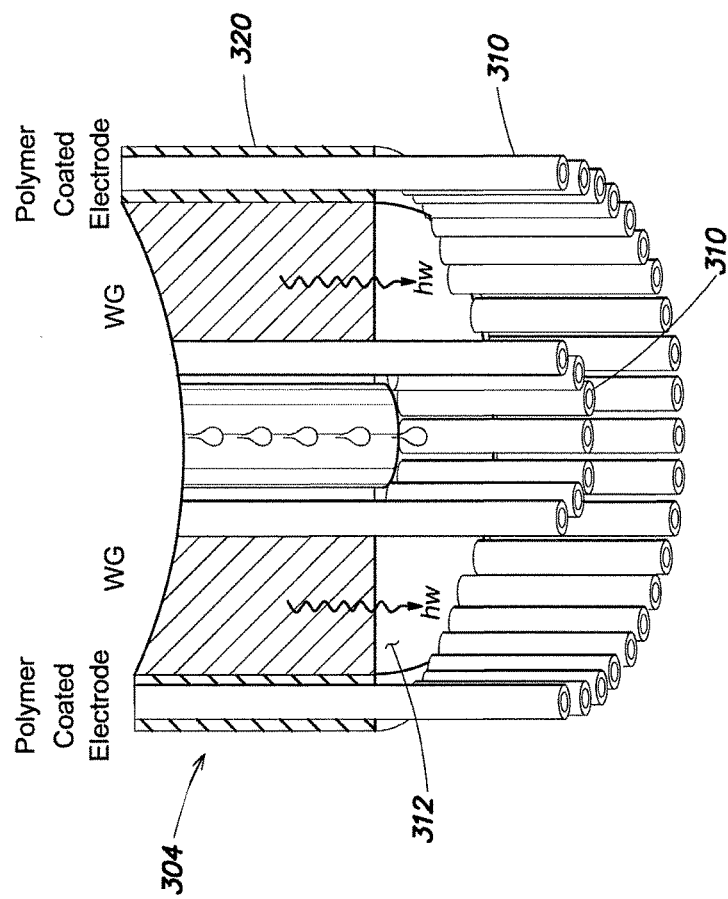

FIG. 3D illustrates a neural probe 304 with conductive fibers 310 arranged in a pair of concentric circles coaxial with the neural probe's longitudinal axis. The inner circle rings a hollow core (lumen) 314 that extends along the neural probe's longitudinal axis for drug delivery, fluid removal, etc. A tubular optical waveguide 312 extends radially between the inner circle and the outer circle.

Those of skill in the art will also readily appreciate that a neural probe may have any suitable number of inner and outer layers, and that each of these layers may have a different cross section and be made of a different material. The conductive fibers may also be made of different materials and have different diameters, cross sections, and impedances. In addition, different conductive fibers may be coated by different types of insulating layers.

Figure 4B:
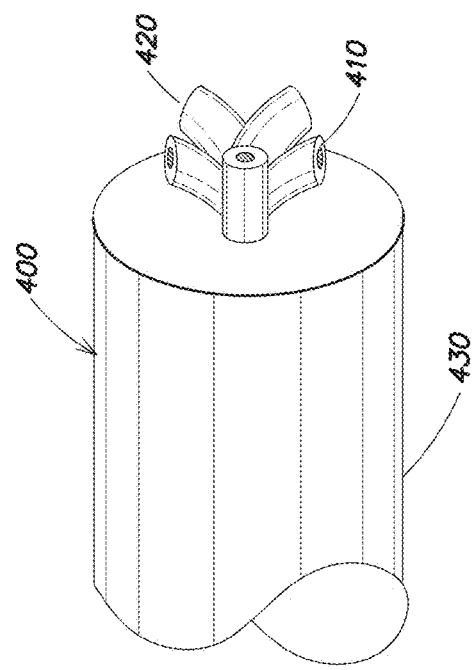
FIGS. 4A and 4B illustrate a neural probe with multiple filaments held together by a water-soluble adhesive before and after, respectively, insertion into neural tissue.
Figure 4A:
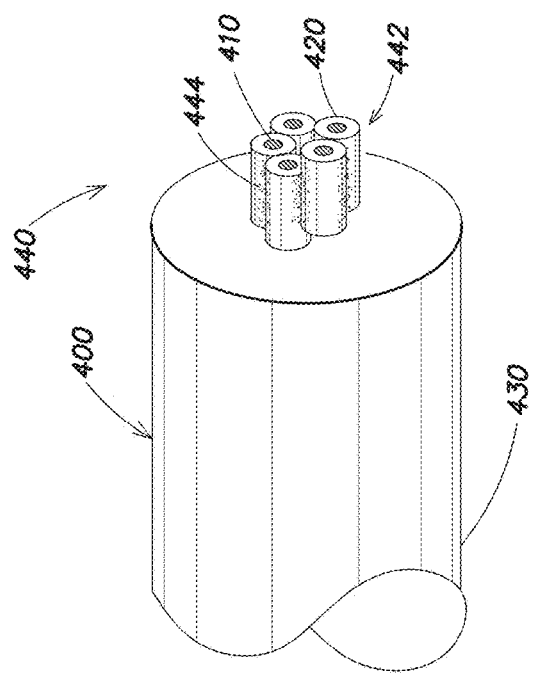

FIGS. 4A and 4B show a neural probe 400 with a biocompatible, water-soluble adhesive 444, such as sucrose, sugar, polyethylene glycol (PEG), silk fibroin, or a polymerized tyrosine derivative, applied to a tip 442 at the neural probe's distal end 440. Like the neural probes described above, the neural probe 400 includes several conductive fibers 410, each of which is coated with at least one respective inner layer 420 of insulating material. One or more outer layers 430 of insulating material surround the inner layers 420. These outer layers 430 are peeled, etched, or stripped away to expose the tip 442, which is inserted into the targeted neural tissue.

Before insertion, the water-soluble adhesive 444 bonds the outer surfaces of the inner layers 420 together to form a tight bundle of insulator-coated conductive fibers 410 at the neural probe's tip 442 as shown in FIG. 4A. Because the conductive fibers 410 are bundled together so tightly, the tip 442 has a smaller profile, which reduces the trauma caused by inserting the tip 442 into the targeted neural tissue. Once the tip 442 has been positioned as desired in the neural tissue, the water-soluble adhesive 444 dissolves, allowing the conductive fibers 410 to move with respect to each other. In some cases, the conductive fibers 410 and/or the inner insulating layers 420 may chosen or constructed to have hysteresis that causes the conductive fibers 410 to splay apart from each other as shown in FIG. 4B. In other cases, the conductive fibers 410 may not be biased towards or away from each other; instead, they may settle or move into positions dictated by the geometry and stiffness of the surrounding tissue.

Thermal Drawing Processes for Making Flexible Neural Probes

An inventive neural probe can be made using a thermal drawing process (TDP) inspired by fabrication techniques for optical fibers. In thermal drawing, a macroscale composite template, also called a pre-form, is fabricated using low-end mechanical processing, then heated and drawn into a fiber with a microscale features. Drawing scales the pre-form's radial dimensions by a reduction factor of 10, 100, 1000, 10000, or more. If desired, the pre-form can be drawn multiple times, allowing the creation of structures on the nanometer scale without the need for high resolution fabrication technology. At the same time, drawing stretches the structure's the length by a factor of 100, yielding a structure that can be hundreds of meters long with a cross section that mimics the cross section of the macroscopic pre-form. Because the neural probe's cross section is a scaled version of the pre-form's cross section, the number, density, and arrangement of the electrodes in the neural probe may be determined by constructing the pre-form appropriately.

Thermal drawing faithfully reproduces the cross-sectional geometry of the macroscopic preform, so it enables the creation of sophisticated multifunctional structures on the microscale without microscale fabrication techniques. Thermal drawing also makes it possible to combine materials with widely varying optical and electrical properties. For example, a single thermally drawn device may include waveguide core and cladding materials, conductive polymer composites, and low-melting temperature metal microwires. As explained above, a neural probe with an optical waveguide and micron-scale electrodes can be used for optogenetic and pharmacological cell identification with long-term electrophysiological recording of the brain during learning and plasticity.

In general, any template made of polymer composites can be thermally drawn, as long as the glass transition temperatures of the template's materials are within 10% of each other. In addition, the material in the template's outermost layer should have a glass transition temperature that is equal to or higher than that of the composite's other materials.

Suitable insulating materials include, but are not limited to polymers such as polycarbonate (PC, $T_M$=140-145°), polysulfone (PSU, $T_M$=185°), cyclic olefin copolymer (COC, $T_M$=150°), poly(etherimide) (PEI, $T_M$=235°), and polyphenylsulfone (PPSU).

In some cases, at least outer layer is formed of a polymer that can be readily etched or dissolved in a given solvent, and at least one inner layer is formed of a polymer, glass, or other material that is not as readily etchable or dissolved in the given solvent. For instance, suitable material outer layer/inner layer combinations include, but are not limited to PC/COC, COC/PC, PPSU/PEI, PEI/PSU, PPSU/PSU, PSU/PC, and PSU/COC. These pairs of materials have comparable glass transition temperatures, which means that thermal behavior does not dictate which polymer is used as the inner layer or the outer layer. COC is more chemically resistant than PC in certain solvents, so PC can be used as the outer layer when etched with these solvents. On the other hand, dichloromethane dissolves PC quickly, but interacts much more slowly (if at all) with COC, which means that COC can be used as an inner layer and PC can be used as an outer layer when etching with dichloromethane. Similarly, PEI is more chemically resistant than PPSU: tetrahydrofuran (THF) dissolves PPSU, but tends not to interact with PEI over the time it takes to dissolve PPSU.

The conductive material's properties also affect the neural probe's construction. In general, the conductive material(s) and the insulating materials should have similar melting temperatures. Suitable conductive materials include, but are not limited to metals, alloys, and conductive polymers, such as tin ($T_M$=232°), silver ($T_M$=962°), indium ($T_M$=157°), gold, platinum, iridium, tungsten, tin-indium, tin-silver, tin-gold, tin-zinc, carbon-loaded polycarbonate (CPC, $T_M$≈230°), polyethylene (CPE, $T_M$≈140°), and polyurethane (CPU, $T_M$≈200°).

In general, the materials for the insulating layers are chosen to have different solubilities or etching properties so that they can be removed selectively from the distal end of the neural probe to form the tip. For instance, the inner layer may be polyurethane (PU), and the outer layer may be COC. PU is commonly used for encapsulation of implantable devices due to its extreme stability in physiological fluids. In addition, PU has low solubility in common organic solvents, whereas COC has relatively high solubility in several common organic solvents, which implies that organic solvents can be used to etch COC layer without removing PU. In fact, experiments indicate that PU remains stable over at least about 24 hours upon exposure to acetone, hexane, chloroform, and dichloromethane, all which can be used to etch COC.

FIGS. 5A-5C illustrate a process of making a macroscopic template suitable for being thermally drawn into a neural probe with multiple metallic electrodes (conductive fibers). The process starts with application of a first (inner) layer of insulating material 520, such as an insulating polymer, to a template of conductive material 510 to form a first pre-form 501 (FIG. 5B). For example, FIG. 5A shows how to make the first pre-form 501 by rolling one or more polymer sheets 520 around a conductive cylindrical rod 510. (Other rod shapes are also possible—e.g., squares, ellipses, stars, etc.) One or more first pre-forms 501 can be disposed inside a second (outer) layer of conductive material 530 as shown in FIG. 5C to form a second pre-form 502 suitable for thermal drawings. As explained in greater detail below, the first pre-form 501 may be drawn and sectioned, then covered with the second layer of conductive material 530.

Alternatively, the first pre-form can be formed by machining a through hole or blind hole (e.g., with a diameter of about 0.25 inches to about 1.0 inches and a depth of about 3 inches to about 4 inches) in a solid polymer cylinder (e.g., with a length of about 5 inches to about 6 inches and a diameter of about 1 inch to about 2 inches). If the hole is a through hole, it may be sealed (e.g., using high temperature resistant epoxy) to prevent the metal from just falling off the preform. Suitable care should be taken when drawing a pre-form sealed with epoxy to prevent the fiber from breaking, to avoid drawing the epoxy, and to avoid forming a metal sphere at the beginning of the draw. A conductive rod (e.g., a conductive polymer or conductive oxide) is inserted into the hole to form a first pre-form, which is annealed (e.g., in low vacuum (<25 Torr) at a temperature of about 140° C. to about 250° C.) to eliminate air pockets that might otherwise form defects in the neural probe. The ratio of the diameters of the polymer cylinder and the conductive rod determines the ratio of the spacing between the electrodes to the electrode size in the neural probe.

Other methods of forming the first and/or second pre-form include, but are not limited to: dip-coating the conductive material or the first pre-form in insulating material; spraying insulating material onto the conductive rod or the first pre-form; sputtering insulating material onto the conductive rod or the first pre-form; depositing insulating material onto the conductive rod or the first pre-form; and painting insulating material onto the conductive rod or the first pre-form.

A hollow channel can be incorporated into the pre-from by using a mandrel during the fabrication of the polymer cladding template. The mandrel is removed before drawing the template, resulting in a hole. In some cases, the lumen diameter may be as small as 20 μm and wall thickness tunable from tens to hundreds of microns, e.g., for confining individual neurons within the lumen as described below. Flowing pressurized inert gas (e.g., nitrogen gas) through the lumen during drawing prevents the lumen from collapsing during the drawing.

Likewise, an optical waveguide can be incorporated by using a different polymer (with a higher refractive index than the cladding and low absorption in the spectral region of interest) instead of a mandrel as explained in greater detail below. To ensure proper thermal drawing, the waveguide material should have glass transition and melting temperatures similar to those of the other materials in the pre-form.

Once the pre-form is complete, it is loaded into a drawing tower 600, where it is suspended vertically and attached to a capstan 620 as shown in FIG. 6. A heating mantle 610 in the drawing tower 600 applies a heat gradient (e.g., of about 300° C. to about 350° C.) uniformly around the circumference about one inch above the pre-form's lower end. The heating mantle 610 heats the pre-form to a first temperature that is higher (e.g., 30% to 80% higher) than both the pre-form's melting temperature and its glass transition temperature. Once the pre-form starts to flow, the pre-form temperature is decreased to second temperature that is lower than the first temperature (e.g., 5% to 30% higher than the higher of the pre-form's melting temperature and its glass transition temperature). The capstan 620 pulls the flowing pre-form at a speed of about 1 m/min and winds the drawn pre-form onto a spool at predetermined drawdown ratio set by. The resulting structure has a diameter of tens to hundreds of microns with a cross section that resembles the cross section of the pre-from. The heating mantle's temperature, feed speed, and tensile stress (which may be about 150 g/mm² to about 1.5 kg/mm²) applied by the capstan 620 to the flowing pre-form affect the exact diameter of the resulting structure and can be set or varied as desired. If desired, the drawn pre-form can be drawn again to further reduce the device diameter.

Figure 7A:
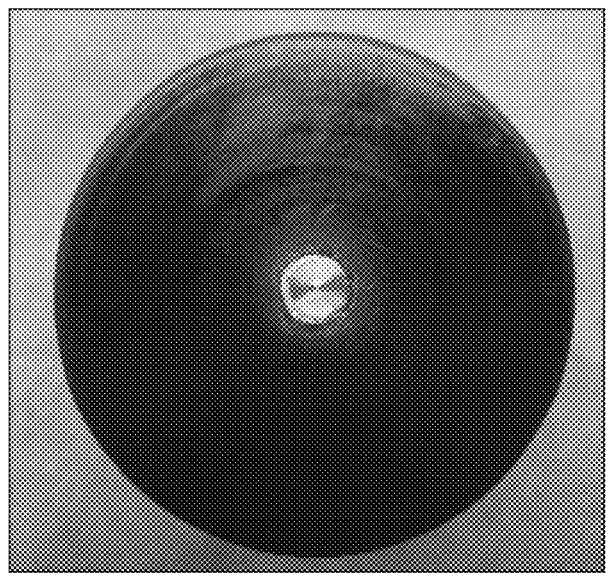
FIG. 7A is a photograph of a macroscopic template (pre-form) with a tin electrode (conductive fiber) surrounded with poly(etherimide) (PEI).
Figure 7B:
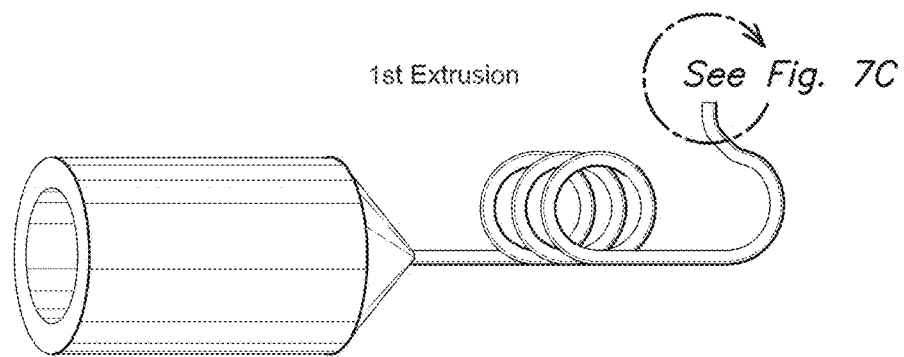
FIG. 7B illustrates the first step of a two-step drawing process using the macroscopic template of FIG. 7A.
Figure 7E:
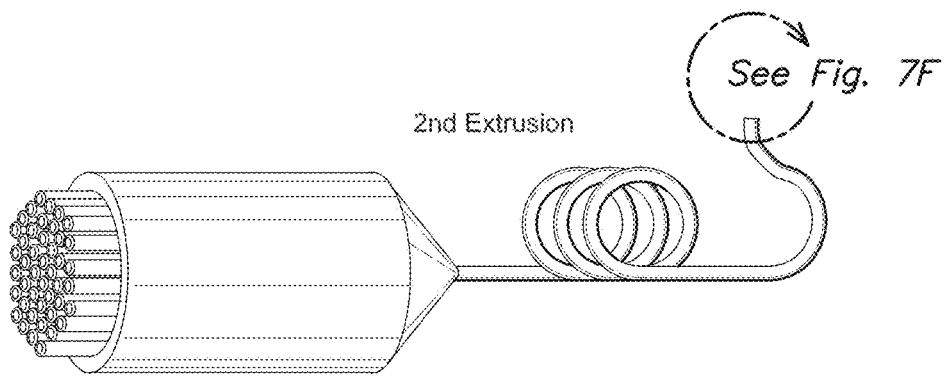
FIG. 7E illustrates the second step of a two-step drawing process using with the composite template of FIG. 7D.
Figure 7C:
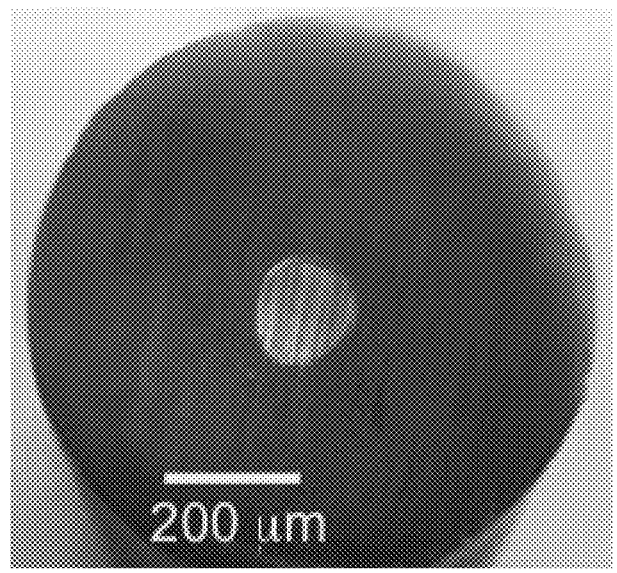
FIG. 7C is an optical microscope image of strand produced by first extrusion step in FIG. 7B.
Figure 7D:
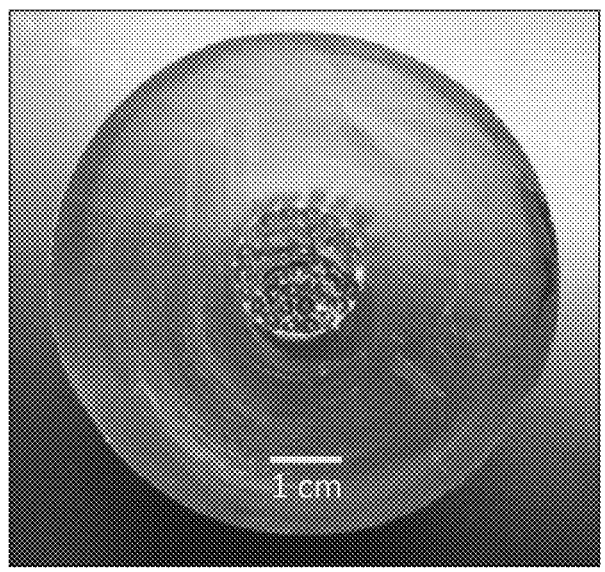
FIG. 7D is an image of a composite template incorporating 36 of the strands show in FIG. 7C surrounding by a layer of poly(etherimide) (PEI).
Figure 7F:
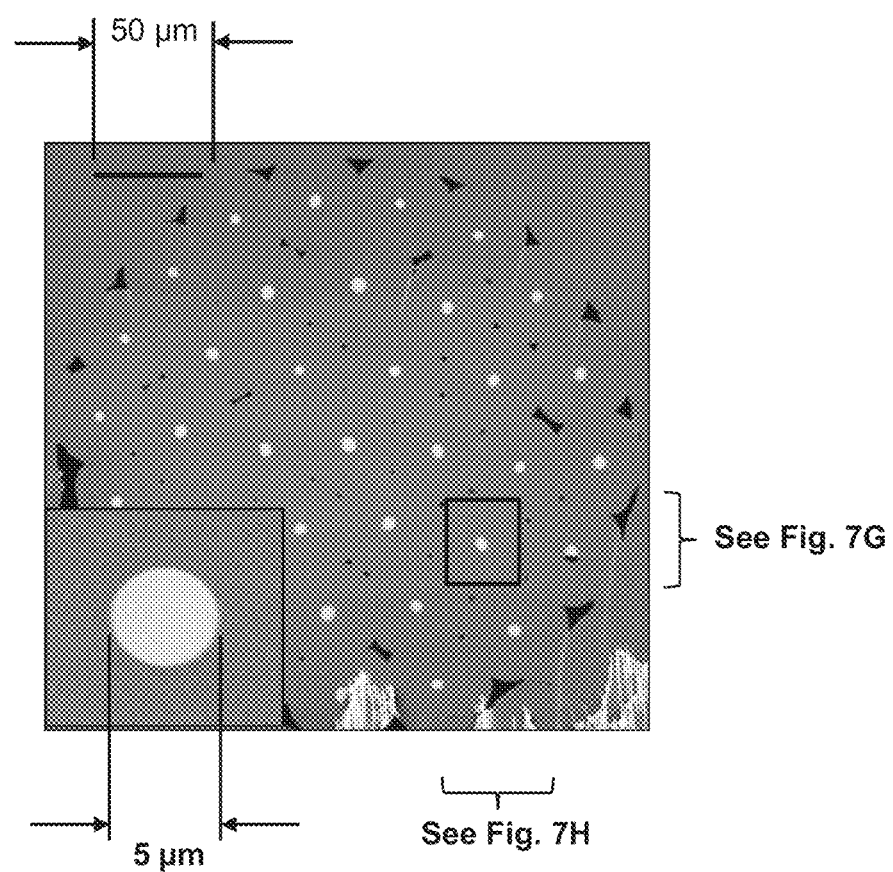
FIG. 7F is a scanning electron micrograph (SEM) of the tip at the distal end of the neural probe produced by extrusion of the composite template in FIG. 7E.
Figure 7G:
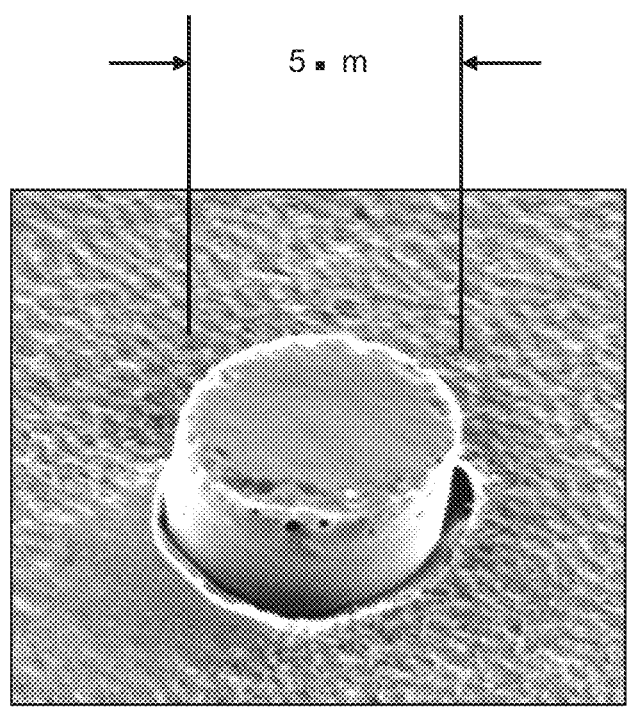
FIG. 7G is an SEM of one of the 5 µm electrodes shown in FIG. 7F.
Figure 7H:
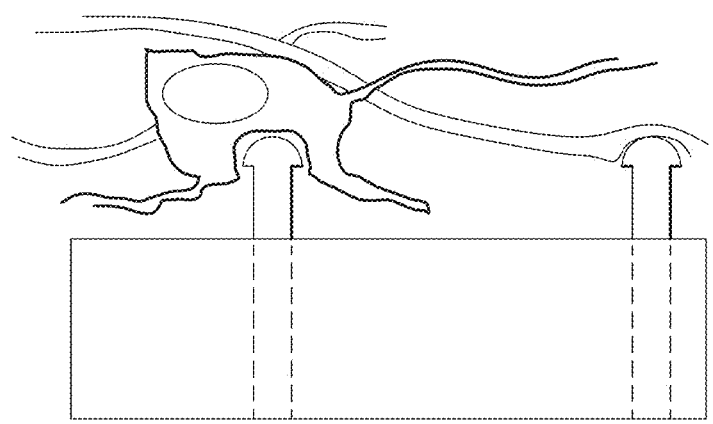
FIG. 7H is a drawing of a nerve cell in contact with the electrode shown in FIG. 7G.

FIGS. 7A-7H illustrate a two-draw process for creating a neural probe. The process begins with covering a conductive material, such as a metal rod, with a polymer cladding (e.g., thin polymer sheets, pre-cut rods, or slabs) and annealing the resulting macroscopic composite template under pressure or vacuum to form the first pre-form shown in FIG. 7A. The first pre-form is then thermally drawn (FIG. 7B) a first time to form a conductive fiber coated with an insulating layer at a desired diameter (FIG. 7C). The resulting fiber is cut into section, which are arranged in an array (e.g., a hexagonal or square array) and covered with another layer of polymer to form a second pre-form (FIG. 7D). The second pre-form may be annealed at a temperature about 1° C. to about 5° C. lower than the melting point of the outermost polymer layer before being drawn to a desired size (e.g., tens to hundreds of microns) as shown in FIG. 7E.

Etching Neural Probe Tips

Once the final thermal drawing step is done, the tip of the drawn structure is etched selectively to remove the outermost layer(s) of insulating material, exposing the electrodes. Etching exposes the electrodes for interactions with neurons. If desired, selected inner layer(s) can be etched as well. Suitable etching techniques include, but are not limited to photolithography, wet etching, plasma etching, and ion milling.

Figure 8A:
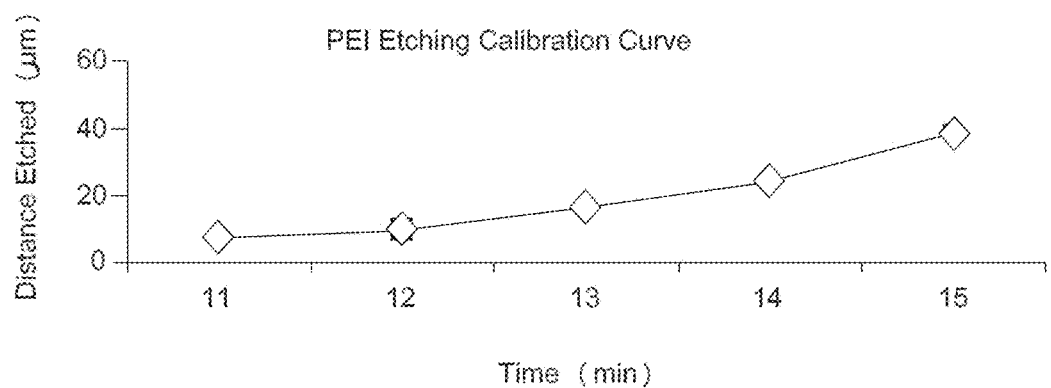
FIGS. 8A and 8B are plots of etch depth versus time for PEI and tin, respectively.
Figure 8B:
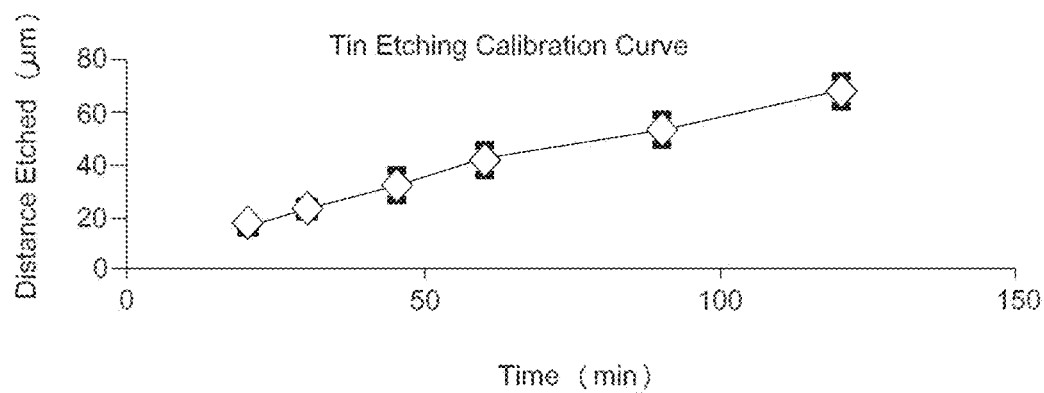

For example, the tip can be formed by coarse wet etching followed by finer oxygen plasma etching. In some examples, wet etching can also be accomplished by dipping the neural probe's distal end into a solvent, such as acetone, methanol, and hydrochloric acid, that dissolves different materials at different rates. Other suitable polymer solvents include THF, dimethyl sulfoxide (DMSO), chloroform, dichloromethane, hexane, benzene, and toluene; glass solvents include HF and agua reggia. For example, FIG. 8A is a plot of etching distance versus time for PEI in a 4:3 volumetric mixture of $CHCl_3$/MeOH, which does not etch tin. It shows that the etching rate for PEI is roughly 7 μm/min. And FIG. 8B is a plot of etching distance versus time for tin in 10 M HCl, which does not etch PEI or other polymers. It shows the etching rate for tin in HCl is about 0.5 μm/min. Thus, $CHCl_3$/MeOH can be used to etch a PEI insulating layer without etching tin electrodes, and HCl can be used to etch tin electrodes without an etching insulating layer made of PEI or any other polymer.

Oxygen plasma etching affects only organic matter at a rate that depends on the polymer's degree of cross-linking and the molecular weight. For example, the oxygen plasma etching rate may be about 0.8 μm/hr±0.1 μm/hr, which is slow enough for very fine etching. Because oxygen plasma etching is so selective and relatively slow, it can be used to polish polymer-polymer interfaces as well as polymer-metal interfaces.

Figure 9:
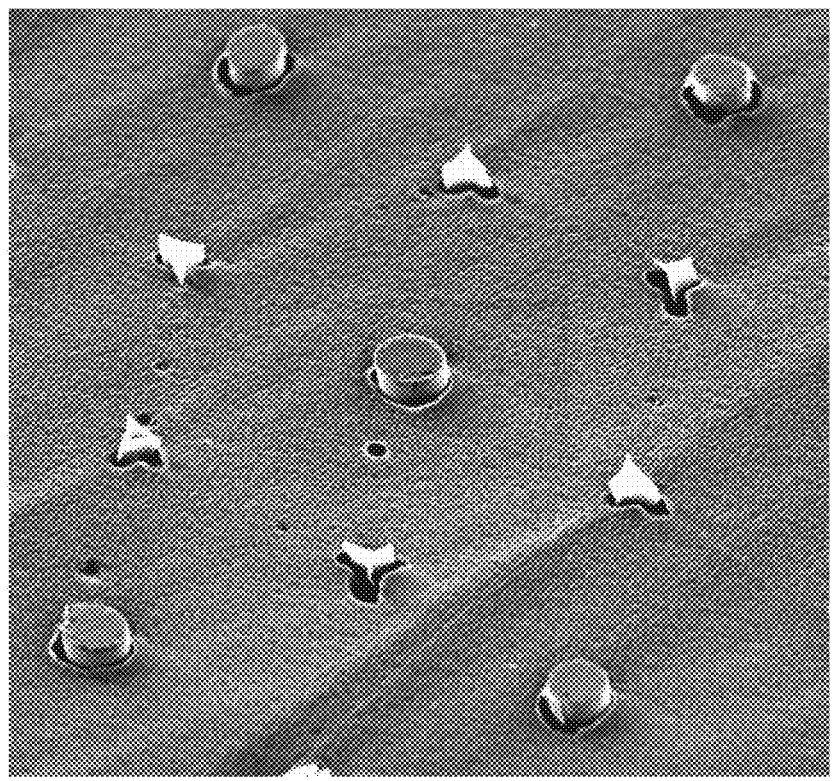
FIG. 9 is a photograph of the tip of an exemplary neural probe after etching.

FIG. 9 is a photograph of a tip of an exemplary neural probe after completion of the etching process. It shows cylindrical electrodes extending from the surface of a polymer layer, which has been partially removed, e.g., by wet etching. (The three-pronged, star-shaped protrusions are residual polymer from the walls of the gaps.) The electrodes can be as small as 2-3 μm in diameter with a size and pitch that can be controlled within ±0.6 μm and ±3 μm by appropriate construction and drawing of the pre-form. At sizes of under about 5 μm, the electrodes may be smaller than the targeted neurons, enabling measurements with high spatial resolution.

If desired, the portions of the electrodes (conductive fibers) exposed by etching can be plated or coated to eliminate direct contact between the conductive material (e.g., tin or tin alloy) and the targeted neural tissue. Plating the electrodes (e.g., with gold) may lower their electrode impedance (e.g., from about 4-10 MΩ to about 150 kΩ to about 1 MΩ). It may also creates a physiologically favorable interface for long-term stability within the tissue. Suitable plating techniques include direct electroplating of a thin gold layer on the surface of the electrodes and down-etching of the electrodes and electrochemically defining gold electrode tips. Alternatively, the electrodes can be coated with gold (or other material) by etching the electrodes into the polymer cladding to form trenches and then filling these trenches with gold via electroplating.

The proximal end of the neural probe may also be etched or processed for connection to an electrical interface (e.g., the electrode interface board 254 shown in FIGS. 2A-2B). For instance, the conductive fibers can be bonded directly to an electrode interface board compatible with a multi-channel neural recording system (e.g., a Tucker Davis Technologies Inc., 32-channel recording system with ZIF headstages). As thermal drawing yields a neural probe that is tens to hundreds of meters long with a highly reproducible cross section, neural probe cross-sectional scanning electron microscope (SEM) images can be used to design a contact mask matched to the specific FINP geometry. The mask is used to lithographically define a pattern of electrodes establishing connections between the conductive fibers and the electrode interface board. The conductive fibers are matched to the electrode interface board using mask-alignment procedures like those used in silicon wafer processing. The electrode interface board is heated using a computer-controlled electrical heating pad to just below the melting point of the electrodes (e.g., about 140° C. for indium). Indium and tin have a eutectic point at 120° C., and consequently upon contact the interface between tin-rich neural probe electrodes melt and are bonded upon cooling akin to conventional soldering. To reduce the possibility of polymer encapsulation during bonding, the electrodes can be exposed during plasma etching.

Making Flexible Neural Probes with Optical Waveguides

Thermal drawing can also be used to make neural probes with integrated optical waveguides and/or lumens. Generally speaking, the optical waveguide materials should be transparent at the desired transmission wavelength. For instance, for optogenetic applications, such as channelrhodopsin 2 (ChR2) facilitated neuronal activation, the waveguide core should have high transmission at a wavelength of 473 nm—the peak wavelength of the ChR2 absorption. The waveguide core should also have a refractive index of the core is greater than that of the waveguide cladding.

In addition, the waveguide materials should glass transition temperatures commensurate with those of the insulating and conductive materials in the neural probe. While majority of polymer waveguides are based on poly(methyl methacrylate) (PMMA, refractive index n=1.49), PMMA has a relatively low glass transition temperature of 105° C. Polycarbonate (PC, n=1.59) and cyclic olefin copolymer (COC, n=1.52) have refractive indices (and melting temperatures) that make them suitable for use as core and cladding, respectively. The high index contrast between a PC core and a COC cladding results in a numerical aperture NA=0.47. This corresponds to a coupling angle of about 56°, which is comparable or higher than that for commercially available multimode silica fibers (NA=0.22-0.37). Calculations also indicate that PC/COC waveguides should, in principle, maintain multimode transmission at core diameters of less than about 10 µm.

In addition to its high refractive index and compatibility with thermal drawing, PC is highly transparent at 473 nm (e.g., loss of <1 dB/cm). This implies that in order to achieve light power densities of about 1-10 mW/mm$^2$, which is commonly cited as sufficient for ChR2-facilitated neural excitation, the optical input power should be about 50 mW for a neural probe length of 1-2 cm. Optical input powers of 50 mW are readily achievable with diode pumped solid state laser systems and other light sources.

Neural Probes with Trapped Biological Cells

A neural probe may also include one or more biological cells, such as neuron cells, renal cells, glial cells, or muscle cells, that are disposed at or near its tip. For instance, the cell may be disposed on an electrode, inside a lumen that extends along the length of the neural probe, or at least partially within a blind hole etched into the tip at the end of an optical waveguide. In some cases, the neuron is within about 500 µm from the neural probe's distal end. The cell can be stimulated electrically by the electrode, with a drug delivered through the lumen, or optically using light guided by the waveguide to interact with the neural tissue. The parallel optical and electrical channels enable simultaneous optical and electrophysiological characterization of individual growing neurons.

For instance, optogenetic manipulation can be used to activate one or more light-sensitive neurons disposed at or near the tip of a neural probe. The light sensitivity of the trapped neurons and the neural probe's ability to guide visible light makes it possible to evoke action potentials from trapped neurons with millisecond precision. As a result, the trapped neurons may be used as relay devices for manipulation of neural activity outside the probe, e.g., via relayed optical excitation or inhibition of genetically-intact neural networks. The trapped neurons may also establish synaptic connections with neurons outside the neural probe. If these connections are formed in damaged neural tissue, the optically sensitive relay neurons may act as growth and development centers within the damaged neural network.

Advantages of using neural probes to host trapped cells compared to traditional, unconstrained tissue culture and flat, silicone elastomer-based microfluidic devices include, but are not limited to: (1) the ability to explore each of the proposed methods for axonal guidance or combine multiple approaches (e.g. optical and electrical) within the same experiment, while simultaneously providing electrophysiological data and optical images; (2) the possibility of relocating and implanting the neural probe; (3) the possibility of using materials with different mechanical and surface charge properties; and (4) the straightforward integration of an optical waveguide with the electrical and fluid connections. These advantages may enable development of medical devices to control and guide new neuronal growth and repair damaged neural circuits.

Figure 10A:
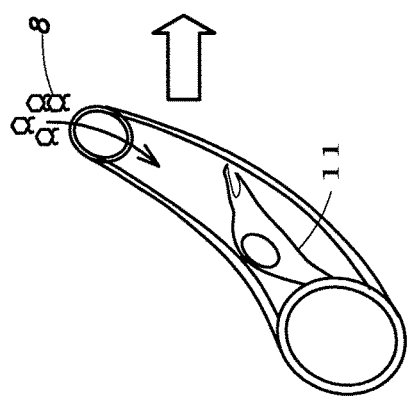
FIGS. 10A-10D illustrates trapping and genetic modification of a neuron trapped within a neural probe, which is used first to synaptically connect the neuron to targeted neural tissue and then to characterize the targeted neural tissue.
Figure 10B:
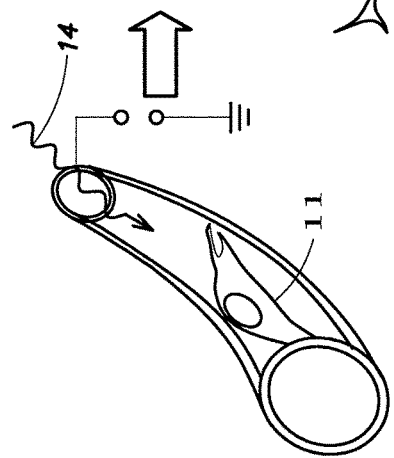
Figure 10C:
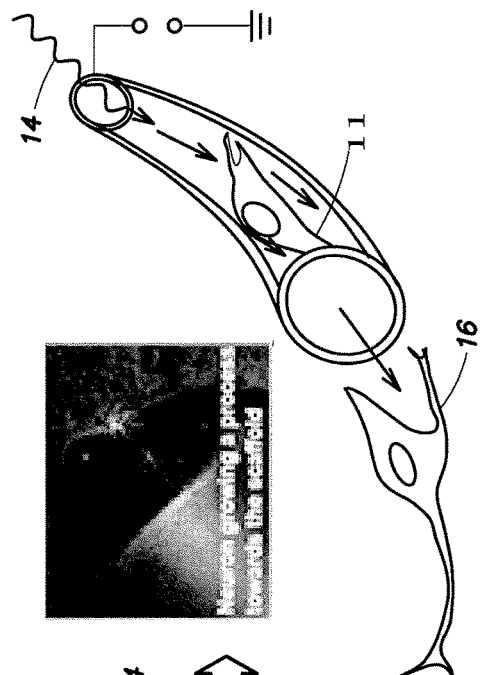
Figure 10D:
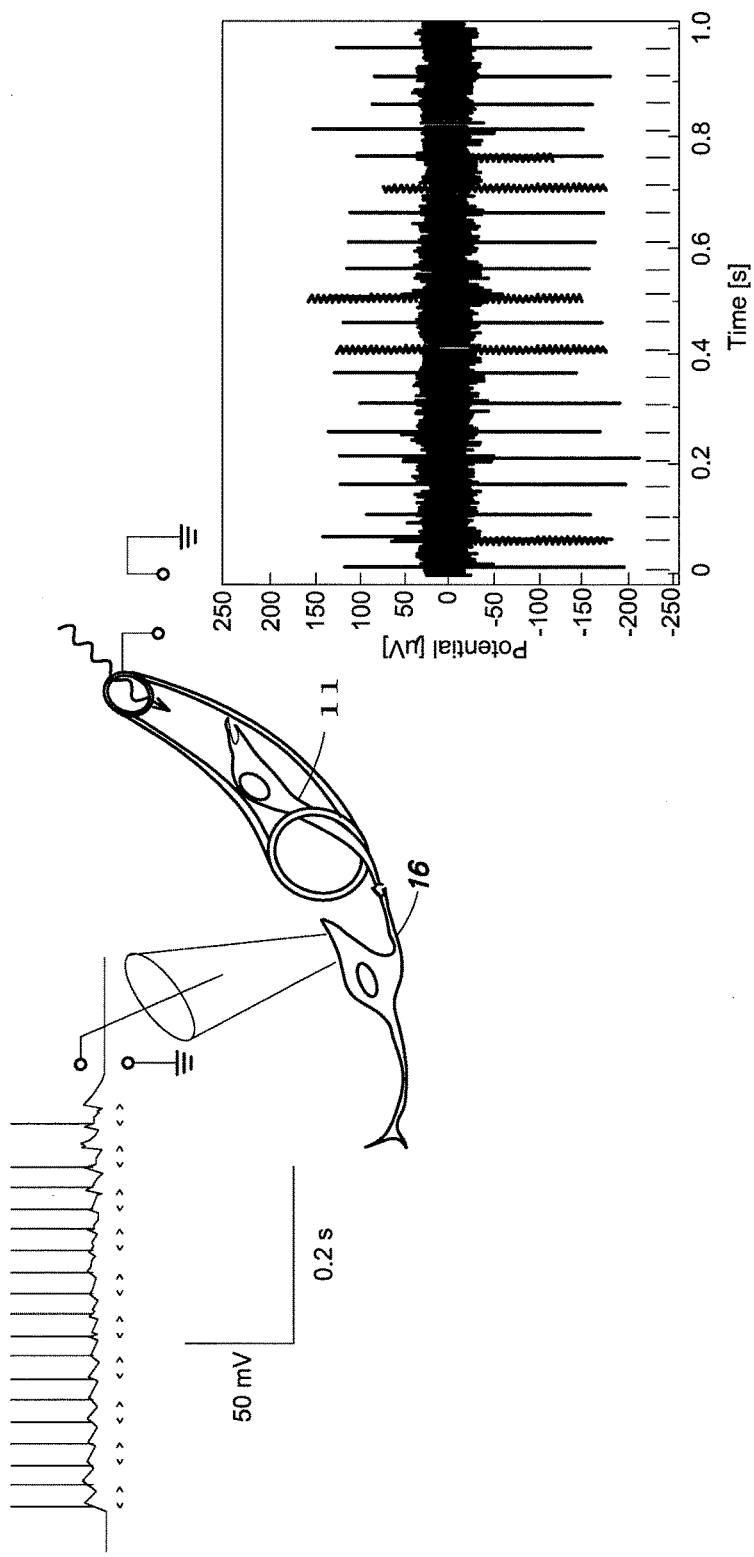

FIGS. 10A-10D illustrates trapping and genetic modification of a neuron 11 trapped within a neural probe 1000, which is used first to synaptically connect the neuron 11 to targeted neural tissue and then to characterize the targeted neural tissue. First, the neuron 11 is trapped within a lumen in the neural probe 1000 (optoelectronic scaffold) using suction, capillary action, electrostatic attraction, or any other suitable technique. Once inside the lumen, the neuron 11 is virally transfected with Channelrhodopsin-2 (ChR2) 14 as shown in FIG. 10A. Channelrhodopsin-2 (ChR2) is a retinal binding, light-activated sodium and calcium ion channel enables sensitivity of neurons to blue light ($\lambda$=473 nm), allowing for excitation of action potentials on demand with light pulses about 0.5-5.0 ms wide at frequencies up to about 50 Hz. Stimulating the transfected neuron 11 with a pulse of blue light 14, as shown in FIG. 10B, causes the neuron 11 to spike. An indigenous neuron 16 establishes a synaptic connection to the trapped neuron 11 in response to the trapped neuron's activity as shown in FIG. 10C. Once the synaptic connection is formed, the neural probe 1000 can be used to trigger the indigenous neuron 16 via optogenetic stimulation of the trapped neuron as shown in FIG. 10D. If desired, this signaling may be used as a part of a brain-machine interface that compensates for or repairs damage to neural tissue.

In order to enable ChR2 expression in trapped neurons, the DNA for ChR2 fused to a fluorescent protein (FP) mCherry or enhanced yellow fluorescent protein (EYFP) is delivered to the neurons via a viral vector. Suitable viral vectors include the herpes simplex virus vector (HSV) and a general cytomegalovirus (CMV) promoter, which yields strong expression in mammalian cells including neurons. Other viral vectors include the Lenti virus and adeno associated viruses (AAVs) as they exhibit low toxicity in multi-week/months optogenetic experiments. The glia population within the neural probe can be controlled using glial inhibition during culture preparation or by employing human synapsin (hSyn) or calmodulin-dependent kinase 2 alpha (CaMKII$\alpha$) promoters to ensure specific targeting to the trapped neurons.

Alternatively, the neuron may be obtained from a transgenic Thy1-COP4/EYFP (Thy1:ChR2) mouse, which expresses ChR2-EYFP fusion in most parts of central and peripheral nervous systems (including hippocampus). A trapped neuron from a transgenic mouse is sensitive to the blue light even prior to seeding within the neural probe.

Trapping Cells at or Near the Neural Probe's Tip

A biological cell, such as a neuron, can be disposed at the neural probe's tip using any suitable technique. For instance, the cells can be suspended in a solution, which is deposited in droplets (e.g., of about 100 µL) at the tip. The solution is sucked into the lumen by applying modest suction through a 1 ml syringe. Alternatively, the solution may wick into the lumen via capillary action. Opposite electric or magnetic charges can be applied to the lumen and the cells, which then become electromagnetically attracted to each other.

The insulating material's electrostatic and chemical properties may also affect the neural probe's ability to hold the neuron. For example, preliminary data suggests that neurons may be more viable and developed within PEI scaffolds than within PC scaffolds. This observation is consistent with the past reports and other data demonstrating viable tissue cultures on positively charged PEI, which has a surface that promotes cell adhesion and growth. The lumen's size and cross-sectional shape may also influence the neuronal viability and growth.

Fluids may also be used to control the neuron's axonal growth. For instance, shear flow may guide the developing axons along the core of the neural probes. Chemicals, such as nerve growth factors, can also be perfused through the lumens that contain neurons at a controlled rate, temperature, and $CO_2$ concentration to influence axonal growth. The neural probe's electrodes and waveguides can be used to collect electrophysiological data and optical measurements of the neuronal growth and activity.

Exemplification

Figure 11A:
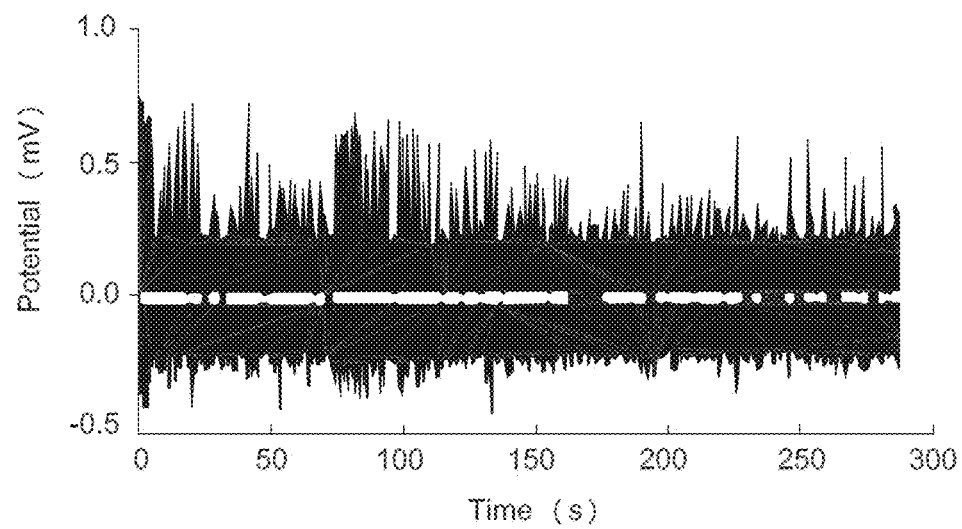
FIG. 11A is a plot of neural activity in the absence of stimulation in the medial prefrontal cortex (mPFC) in an anesthetized 8-week old Thy 1:18 ChR2-expressing transgenic male mouse obtained with a neural probe having 5 µm electrodes in a 36-electrode array.
Figure 11B:
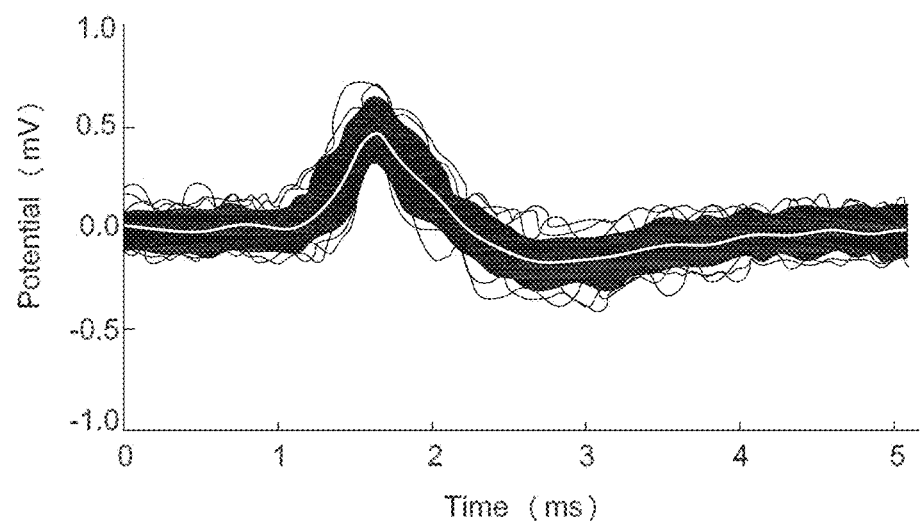
FIG. 11B is a plot of action potential shapes of the higher-amplitude spike shown in FIG. 11A.
Figure 11C:
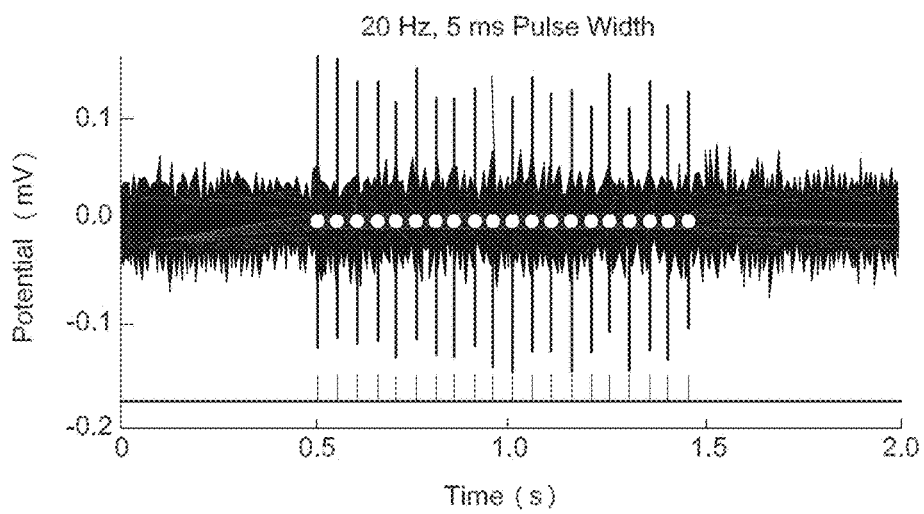
FIG. 11C is a plot of multi-unit response to 20 Hz optical stimulation at a wavelength of 473 nm laser, pulse power of about 7 mW, and a pulse width of 5 ms recorded with the mouse/probe setup of FIG. 11A.
Figure 11D:
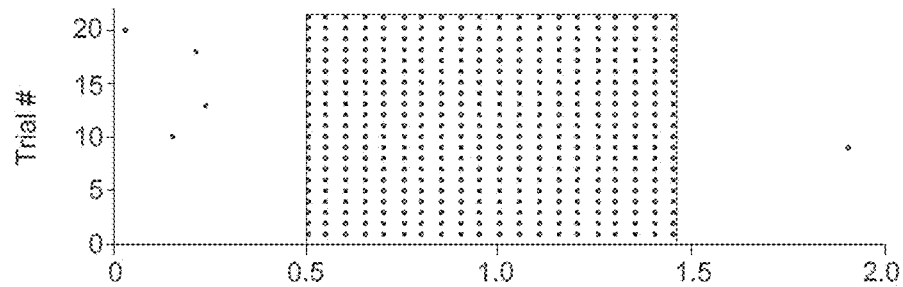
FIG. 11D is a plot of multi-unit spikes in response to optical pulses across 20 trials identical to the trial represented in FIG. 11C.
Figure 11E:
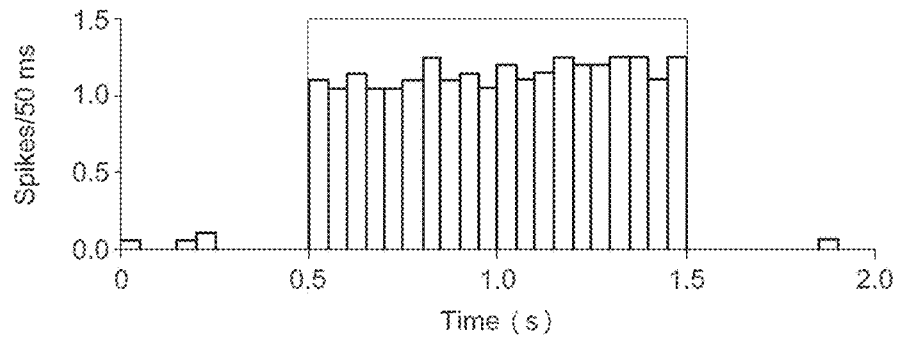
FIG. 11E is a plot of the multi-unit firing rate averaged across the 20 trials represented in FIG. 11D.
Figure 11F:
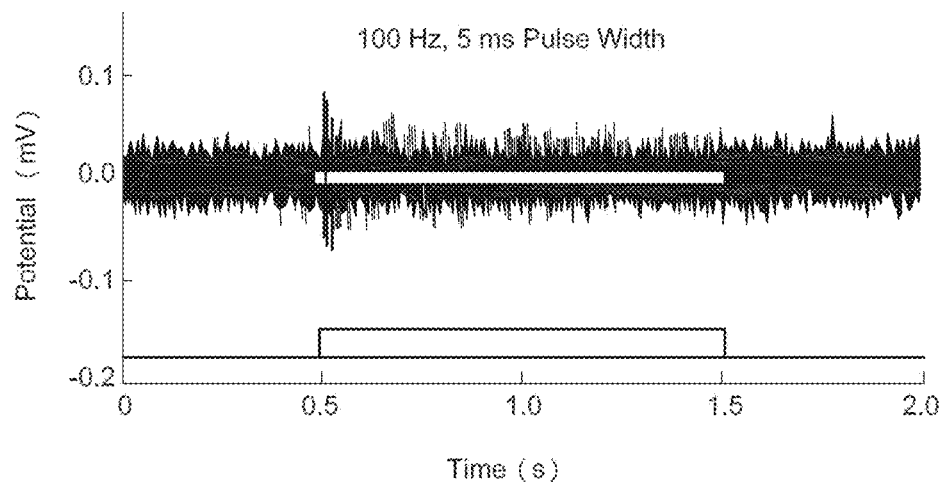
FIG. 11F is a plot of multi-unit response to 100 Hz optical stimulation at a wavelength of 473 nm laser, pulse power of about 7 mW, and a pulse width of 5 ms recorded with the mouse/probe setup of FIG. 11A.
Figure 11G:
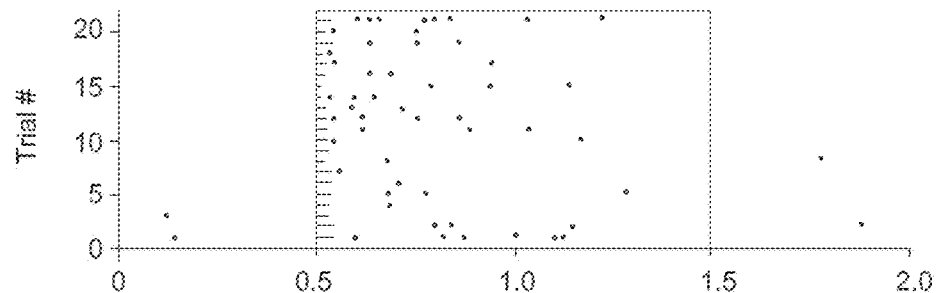
FIG. 11G is a plot of multi-unit spikes in response to optical pulses across 20 trials identical to the trial represented in FIG. 11F.
Figure 11H:
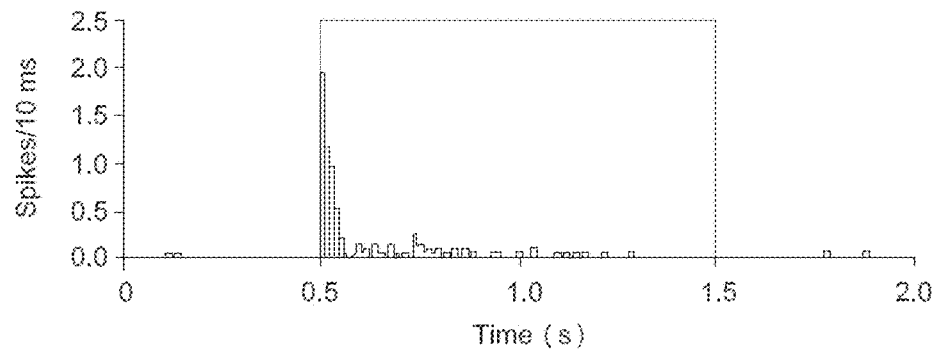
FIG. 11H is a plot of the multi-unit firing rate averaged across the 20 trials represented in FIG. 11G.

FIGS. 11A-11H are plots of representing optogenetically stimulated single-unit activity in the medial prefrontal cortex (mPFC) of anesthetized mice recorded using an exemplary neural probe. More specifically, the neural probe recorded neural activity during optical stimulation with 473 nm laser light in mPFC of transgenic Thy1-ChR2-YFP mice expressing ChR2 across the entire nervous system. FIGS. 11A and 11B are electrophysiological traces that confirm the neural probe's ability to record well-isolated action potentials. FIGS. 5C-5H are plots of recordings at intermediate (20 Hz, FIGS. 5C-5E) and high (100 Hz, FIGS. 5F-5H) stimulation frequencies that show the neural probe is not susceptible to optical artifacts. They show neural activity precisely following the 20 Hz stimulation but not the 100 Hz stimulation, which is consistent with ChR2 dynamics and previous recordings obtained with conventional tetrode probes. The observed initial excitation followed by decline of neural activity during 100 Hz stimulation agrees with previous experiments, which demonstrated the ChR2-facilitated silencing in broad neuronal populations during high-frequency optical stimulation.

Figure 12A:
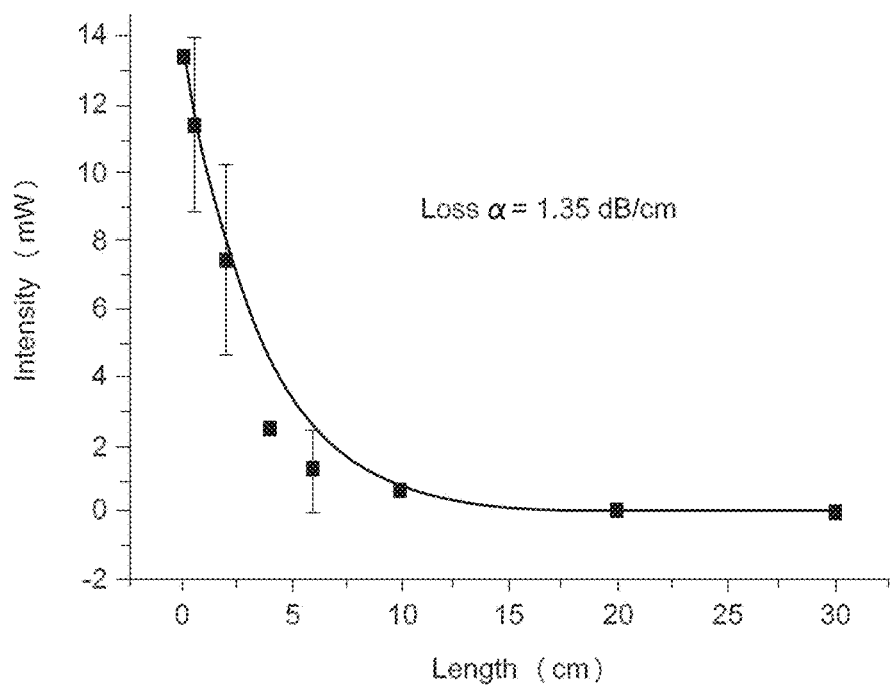
FIG. 12A is a plot of transmitted intensity versus waveguide length for a polycarbonate (PC)/cyclic olefin copolymer (COC) waveguide in a neural probe.
Figure 12B:
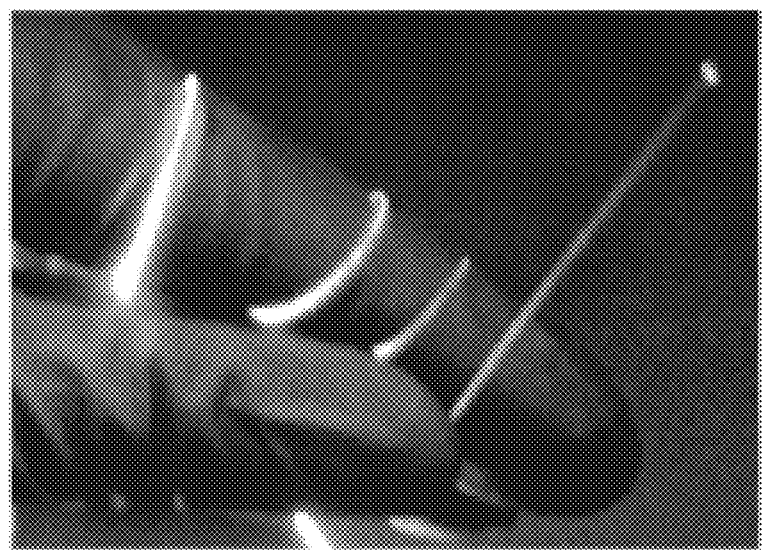
FIG. 12B is a picture of the PC/COC waveguide of FIG. 12A partially guiding light.
Figure 12C:
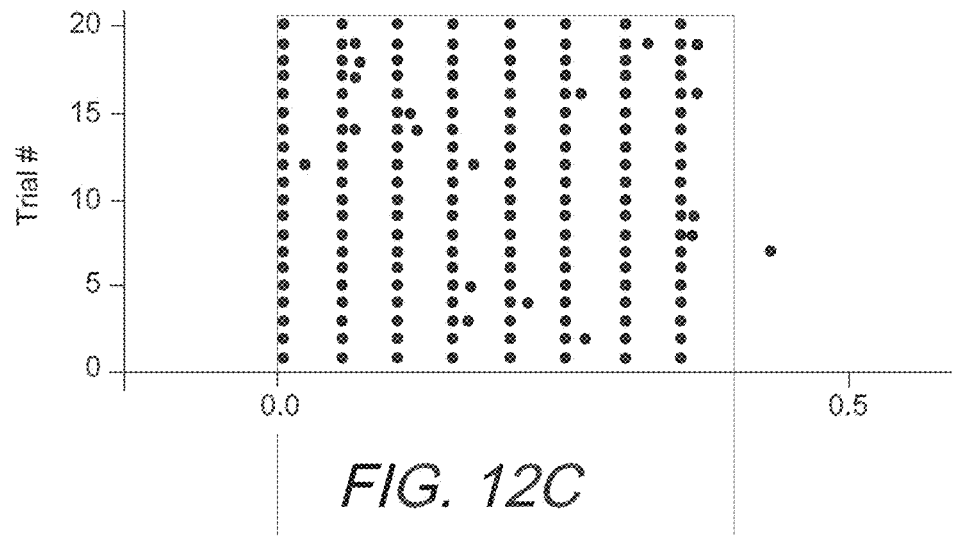
FIG. 12C is a plot of action potentials evoked in an anesthetized Thy1-ChR2-YFP mouse in 20 trials using optical stimulation at 20 Hz via the waveguide of FIGS. 12A and 12B.
Figure 12D:
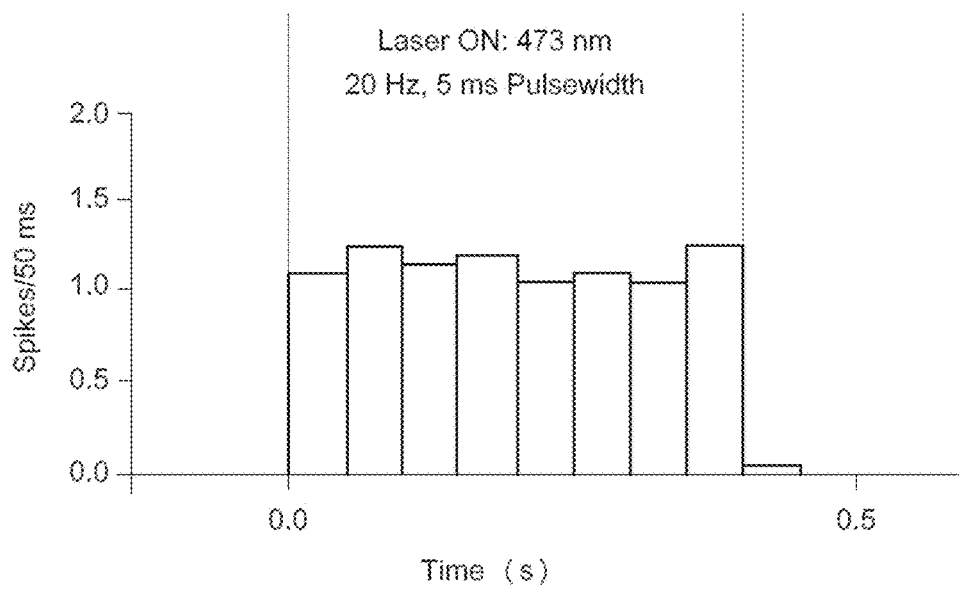
FIG. 12D is a plot of the evoked firing rate averaged across the 20 trials represented in FIG. 12C.
Figure 12E:
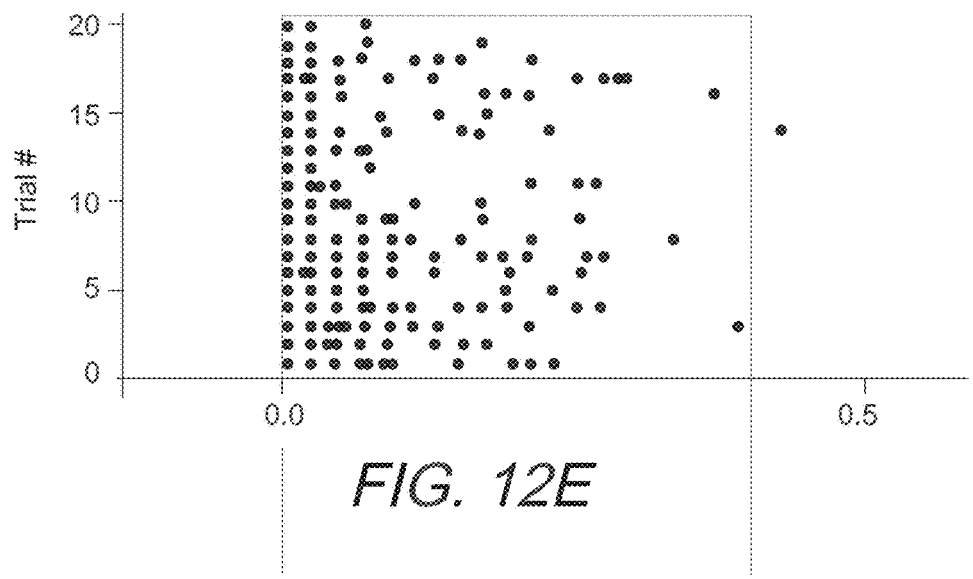
FIG. 12E is a plot of action potentials evoked in 20 trials of the mouse of FIG. 12C using optical stimulation at 50 Hz via the waveguide of FIGS. 12A and 12B.
Figure 12F:
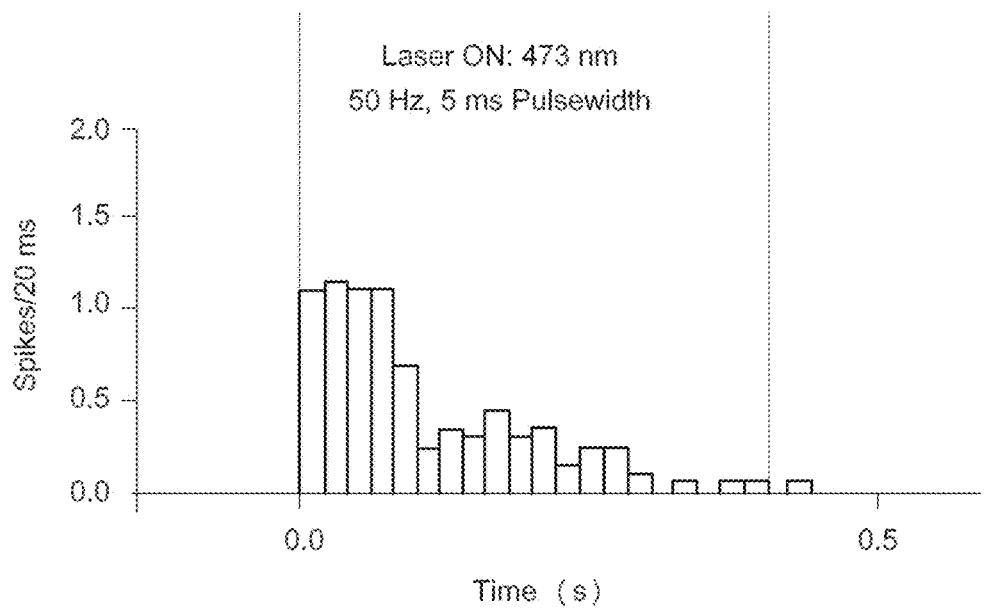
FIG. 12F is a plot of the evoked firing rate averaged across the 20 trials represented in FIG. 12E.

FIGS. 12A and 12C-12F illustrate the function of a PC/COC waveguide (shown in FIG. 12B) in a neural probe. FIG. 12A shows transmitted intensity versus waveguide length at a wavelength of about 473 nm; the loss is about 1.35 dB/cm. FIG. 12C is a plot of action potentials (spikes) evoked by 20 trials of optical stimulation at 20 Hz in an anesthetized Thy1-ChR2-YFP mouse. FIG. 12D shows the evoked firing rate averaged across the 20 trials represented in FIG. 12C. FIG. 12E is a plot of spikes evoked by optical stimulation at 50 Hz in 20 trials in the same mouse using the same neural probe. FIG. 12F shows the evoked firing rate averaged across the 20 trials represented in FIG. 12E.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the coupling structures and diffractive optical elements disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the coupling structures and diffractive optical elements disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A neural probe to probe neural tissue, the neural probe comprising:
    at least one outer insulating layer;
    at least one inner insulating layer, disposed within the at least one outer insulating layer and projecting out of the at least one outer insulating layer to form a tip at a distal end of the neural probe, the tip having an outer diameter of less than about 500 μm;
    at least one conductive fiber, disposed within the at least one inner insulating layer, to conduct at least one electrical signal between a proximal end of the neural probe and the distal end of the neural probe; and
    a mammalian cell, separate from the neural tissue and trapped on or within the distal end of the neural probe, to interact with the neural tissue.

2. The neural probe of claim 1, wherein:
    the at least one conductive fiber comprises a plurality of conductive fibers; and
    the at least one inner insulating layer comprises a plurality of inner insulating layers respectively disposed about a corresponding conductive fiber of the plurality of conductive fibers.

3. The neural probe of claim 2, further comprising:
    a soluble adhesive, disposed on a surface at the tip of the neural probe, to secure a first conductive fiber of the plurality of conductive fibers to a second conductive fiber of the plurality of conductive fibers during insertion of the neural probe into tissue.

4. The neural probe of claim 1, wherein an impedance of the at least one conductive fiber at the distal end of the neural probe is about 150 kΩ to about 10 MΩ.

5. The neural probe of claim 4, wherein the impedance of the at least one conductive fiber at the distal end of the neural probe is about 150 kΩ to about 3 MΩ.

6. The neural probe of claim 1, wherein the at least one conductive fiber comprises at least one of tin, tin-indium, tin-silver, tin-gold, tin-zinc, gold, silver, platinum, iridium, tungsten, conductive polyethylene, conductive polycarbonate, or conductive polyurethane.

7. The neural probe of claim 1, wherein at least one of the at least one inner insulating layer or the at least one outer insulating layer comprises a polymer.

8. The neural probe of claim 1, wherein the at least one inner insulating layer has a first solubility and the at least one outer insulating layer has a second solubility different than the first solubility.

9. The neural probe of claim 1, wherein the at least one inner insulating layer has a first molecular weight and the at least one outer insulating layer has a second molecular weight different than the first molecular weight.

10. The neural probe of claim 1, further comprising:
at least one optical fiber, disposed within the at least one outer insulating layer, to guide electromagnetic radiation between the proximal end of the neural probe and the distal end of the neural probe.

11. The neural probe of claim 1, wherein the neural probe further defines a hollow lumen, disposed within the at least one outer insulating layer, to facilitate transport of a fluid between the proximal end of the neural probe and the distal end of the neural probe.

12. The neural probe of claim 1,
wherein the mammalian cell is trapped within a lumen or cavity defined by the neural probe within about 500 µm of the distal end of the neural probe.

13. The neural probe of claim 12,
wherein at least one of the at least one conductive fiber, an optical fiber, or the lumen defines a channel configured to transmit at least one of stimulation to the mammalian cell or a physiological response of the mammalian cell to interaction with the neural tissue.

14. The neural probe of claim 1, wherein the mammalian cell is a transfected mammalian cell.

15. The neural probe of claim 1, wherein the mammalian cell is at least one of a neuron cell, a renal cell, a glial cell, or a muscle cell.

16. The neural probe of claim 1, wherein the mammalian cell is from an animal.

17. A method of making the neural probe of claim 1, the method comprising:
(A) disposing a first insulating material about an outer surface of at least one conductive rod so as to form a first pre-form;
(B) disposing a second insulating material different than the first insulating material about an outer surface of the first pre-form so as to form a second pre-form;
(C) drawing the second pre-form so as to form a coated conductive fiber;
(D) removing at least a portion of the second insulating material from a distal end of the coated conductive fiber so as to form the neural probe; and
(E) trapping the mammalian cell on or within the distal end of the neural probe.

18. The method of claim 17, wherein (A) comprises at least one of:

(A1) dip-coating the conductive rod in the first insulating material;
(A2) wrapping a sheet of the first insulating material around the conductive rod;
(A3) spraying the first insulating material onto the conductive rod;
(A4) inserting the conductive rod into a lumen formed by the first insulating material;
(A5) sputtering the first insulating material onto the conductive rod;
(A6) depositing the first insulating material onto the conductive rod; or
(A7) painting the first insulating material onto the conductive rod.

19. The method of claim 17, wherein (B) further comprises:
(B1) drawing the first pre-form to form a drawn pre-form;
(B2) sectioning the drawn pre-form into a plurality of segments; and
(B3) disposing the second insulating material about at least some of the plurality of segments to form the second pre-form.

20. The method of claim 17, wherein (B) further comprises disposing the second insulating material about an outer surface of an optical fiber pre-form.

21. The method of claim 17, wherein (B) further comprises disposing the second insulating material about an outer surface of a structure defining a hollow lumen.

22. The method of claim 17, wherein (C) further comprises:
(C1) heating the second pre-form to a first temperature above a first temperature higher than both a melting temperature of the second pre-form and a glass transition temperature of the second pre-form;
(C2) heating the second pre-form to a second temperature below the first temperature; and
(C3) drawing the second pre-form at a predetermined drawdown ratio.

23. The method of claim 22, wherein:
the first temperature is about 30% to about 80% above the higher of the melting temperature of the second pre-form and the glass transition temperature of the second pre-form, and
the second temperature is about 5% to about 30% above the higher of the melting temperature of the second pre-form and the glass transition temperature of the second pre-form.

24. The method of claim 22, wherein (C3) further comprises applying a stress of about 150 g/mm$^2$ to about 1.5 kg/mm$^2$ to the second pre-form.

25. The method of claim 17, wherein (D) further comprises at least one of:
(D1) dissolving at least a portion of the second insulating material at the distal end of the neural probe in a solvent;
(D2) etching at least a portion of the second insulating material at the distal end of the neural probe; or
(D3) stripping at least a portion of the second insulating material at the distal end of the neural probe based on a difference in molecular weight between the first insulating layer and the second insulating layer.

26. The method of claim 17, wherein (E) comprises at least one of:
disposing the mammalian cell on the tip of the neural probe; or disposing the mammalian cell in a cavity or lumen defined by the neural probe within about 500 μm of the distal end of the neural probe.

27. A method of interfacing with neural tissue, the method comprising:
- inserting a distal end of a neural probe into the neural tissue, the neural probe comprising:
  - at least one outer insulating layer;
  - at least one inner insulating layer, disposed within the outer insulating layer and projecting out of the outer insulating layer to form a tip with an outer diameter of less than about 500 μm at the distal end of the neural probe; and
  - at least one conductive fiber, disposed within the at least one inner insulating layer, to conduct at least one electrical signal between a proximal end of the neural probe and the distal end of the neural probe; and
- stimulating a mammalian cell, separate from the neural tissue and trapped on or within the distal end of the neural probe, with at least one of an electromagnetic signal and a chemical.

28. The method of claim 27, further comprising:
recording at least one electrical signal conducted via the at least one conductive fiber.

29. The method of claim 27, further comprising:
guiding electromagnetic radiation between the proximal end of the neural probe and a selected portion of the neural tissue via an optical fiber disposed within the at least one outer insulating layer of the neural probe.

30. The method of claim 27, further comprising:
delivering fluid to a selected portion of the neural tissue via a hollow lumen disposed within the at least one outer insulating layer of the neural probe.

31. The method of claim 27, further comprising:
removing fluid from a selected portion of the neural tissue via a hollow lumen disposed within the at least one outer insulating layer of the neural probe.

* * * * *